(12) United States Patent
Aoki et al.

(10) Patent No.: US 9,988,415 B2
(45) Date of Patent: Jun. 5, 2018

(54) GLYCOSIDE COMPOUND, METHOD FOR PRODUCING THIOETHER, ETHER, METHOD FOR PRODUCING ETHER, METHOD FOR PRODUCING GLYCOSIDE COMPOUND, METHOD FOR PRODUCING NUCLEIC ACID

(71) Applicant: BONAC CORPORATION, Kurume-shi, Fukuoka (JP)

(72) Inventors: Eriko Aoki, Kurume (JP); Hiroshi Suzuki, Fukuoka (JP); Akihiro Itoh, Kurume (JP)

(73) Assignee: BONAC CORPORATION, Kurume (JP)

( * ) Notice: Subject to any disclaimer, the term of this patent is extended or adjusted under 35 U.S.C. 154(b) by 15 days.

(21) Appl. No.: 15/060,152

(22) Filed: Mar. 3, 2016

(65) Prior Publication Data

US 2016/0176810 A1    Jun. 23, 2016

Related U.S. Application Data

(62) Division of application No. 14/240,638, filed as application No. PCT/JP2012/071517 on Aug. 24, 2012, now Pat. No. 9,481,702.

(30) Foreign Application Priority Data

Aug. 25, 2011 (JP) ................. 2011-184196

(51) Int. Cl.

| C07C 323/25 | (2006.01) |
|---|---|
| C07C 323/12 | (2006.01) |
| C07C 319/16 | (2006.01) |
| C07C 319/20 | (2006.01) |
| C07C 319/14 | (2006.01) |
| C07H 19/06 | (2006.01) |
| C07H 21/00 | (2006.01) |
| C07H 23/00 | (2006.01) |
| C07H 1/00 | (2006.01) |
| C07H 19/16 | (2006.01) |
| C07H 19/167 | (2006.01) |
| C07H 19/067 | (2006.01) |

(52) U.S. Cl.
CPC ........... *C07H 19/06* (2013.01); *C07C 319/14* (2013.01); *C07C 319/16* (2013.01); *C07C 319/20* (2013.01); *C07C 323/12* (2013.01); *C07C 323/25* (2013.01); *C07H 1/00* (2013.01); *C07H 19/067* (2013.01); *C07H 19/16* (2013.01); *C07H 19/167* (2013.01); *C07H 21/00* (2013.01); *C07H 23/00* (2013.01); *Y02P 20/55* (2015.11)

(58) Field of Classification Search
CPC ... C07C 323/25; C07C 323/12; C07C 319/16; C07C 319/20; C07C 319/14
See application file for complete search history.

(56) References Cited

U.S. PATENT DOCUMENTS

| 7,569,685 B2 | 8/2009 | Sekine et al. |
|---|---|---|
| 8,691,970 B2 | 4/2014 | Ohgi et al. |
| 2003/0229220 A1 | 12/2003 | Ravikumar et al. |
| 2007/0282097 A1 | 12/2007 | Ohgi et al. |
| 2008/0021206 A1 | 1/2008 | Sekine et al. |

FOREIGN PATENT DOCUMENTS

| CN | 101048423 A | 10/2007 |
|---|---|---|
| EP | 0 639 577 A1 | 2/1995 |
| EP | 1 795 536 A1 | 6/2007 |
| JP | H07-149779 A | 6/1995 |
| JP | 2000-509724 A | 8/2000 |
| JP | 2003-513883 A | 4/2003 |
| WO | WO 1998/029429 A1 | 7/1998 |
| WO | WO 2000/068241 A1 | 11/2000 |
| WO | WO 2005/085271 A | 9/2005 |
| WO | WO 2006/022323 A1 | 3/2006 |
| WO | WO 2006/095739 A1 | 9/2006 |
| WO | WO 2008/090829 A1 | 7/2008 |

OTHER PUBLICATIONS

Wuts et al., Greene's Protective Groups in Organic Chemistry, 2007, John Wiley & Sons, Inc., 4th ed., p. 1-74.*
U.S. Appl. No. 14/240,638, filed Feb. 24, 2014.
Allen et al., *Journal of the Chemical Society*, Section C, 20: 3454-3466 (1971).
Glen Research, "Procedure for the Synthesis, Deprotection and Isolation of RNA using TOM-Protected Monomers," URL: http://www.glenresearch.comTechnicalTB_RNA_TOM_Deprotection.pdf (May 2009).
Iovu et al., *Revista de Chimie*, 34(9): 795-801 (1983).
Mamedov et al., "Synthesis of β-alkylthioethylesters of 2,4-dichlorophenoxyacetic acid," *Doklady—Akademiya Nauk Azerbaidzhanskoi SSR*, 28(1): 15-18 (1972).
Munavalli et al., "Reaction of Epoxides with (Alkylthio)methyl Chloride," *Phosphorus, Sulfur, and Silicon and The Related Elements*, 180(12): 2689-2700 (2005).

(Continued)

*Primary Examiner* — Jonathan S Lau
(74) *Attorney, Agent, or Firm* — Leydig, Voit & Mayer, Ltd.

(57) ABSTRACT

The invention provides a glucoside compound, which is capable of providing a phosphoramidite, which can be produced at low cost and can produce a nucleic acid in high yield and with high purity. The glycoside compound has the formula

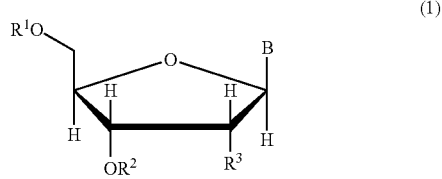

(1)

wherein B, R1, R2, and R3 are as described herein.

8 Claims, 3 Drawing Sheets

(56) References Cited

OTHER PUBLICATIONS

Ohgi et al., *Organic Letters*, 7(16): 3477-3480 (2005).
Pav et al., *Organic and Bimolecular Chemistry*, 9: 6120-6126 (2011).
Wadsworth et al., *Journal of Organic Chemistry*, 47(9): 1623-1626 (1982).
Zhou et al., *Organic and Bimolecular Chemistry*, 5: 333-343 (2007).
Chinese Office Action, Notification of First Office Action in Chinese Patent Application No. 201280052136.6 (dated Feb. 28, 2015).
European Patent Office, Supplementary Partial European Search Report in European Patent Application No. 12825586 (dated Feb. 3, 2015).
European Patent Office, Supplementary European Search Report in European Patent Application No. 12825586 (dated Jun. 18, 2015).
Japanese Patent Office, International Search Report in International Patent Application No. PCT/JP2012/071517 (dated Sep. 25, 2012).

* cited by examiner

SEQUENCE LISTING

<160> NUMBER OF SEQ ID NOS: 4

<210> SEQ ID NO 1
<211> LENGTH: 40
<212> TYPE: RNA
<213> ORGANISM: Artificial Sequence
<220> FEATURE:
<223> OTHER INFORMATION: Synthetic polyuridine

<400> SEQUENCE: 1
uuuuuuuuuu uuuuuuuuuu uuuuuuuuuu uuuuuuuuuu                             40

<210> SEQ ID NO 2
<211> LENGTH: 62
<212> TYPE: RNA
<213> ORGANISM: Artificial Sequence
<220> FEATURE:
<223> OTHER INFORMATION: Synthetic nucleic acid molecule

<400> SEQUENCE: 2
auacuauucg acacgcgaag uuccccacac cggaacuucg cgugucgaau aguauucuuc        60
gg                                                                      62

```
<210> SEQ ID NO 3
<211> LENGTH: 62
<212> TYPE: RNA
<213> ORGANISM: Artificial Sequence
<220> FEATURE:
<223> OTHER INFORMATION: Synthetic nucleic acid molecule

<400> SEQUENCE: 3
agcagcugua cauugacuuu agccccacac cggcuaaagu caauguacag cugcuucuuc      60
gg                                                                    62

<210> SEQ ID NO 4
<211> LENGTH: 21
<212> TYPE: RNA
<213> ORGANISM: Artificial Sequence
<220> FEATURE:
<223> OTHER INFORMATION: Synthetic nucleic acid molecule

<400> SEQUENCE: 4
cuucgcgugu cgaauaguau u                                               21
```

GLYCOSIDE COMPOUND, METHOD FOR PRODUCING THIOETHER, ETHER, METHOD FOR PRODUCING ETHER, METHOD FOR PRODUCING GLYCOSIDE COMPOUND, METHOD FOR PRODUCING NUCLEIC ACID

CROSS-REFERENCE TO RELATED APPLICATIONS

This patent application is a divisional of copending U.S. patent application Ser. No. 14/240,638, filed on Feb. 24, 2014, which is the U.S. national phase of International Patent Application No. PCT/JP2012/071517, filed on Aug. 24, 2012, which claims the benefit of Japanese Patent Application No. 2011-184196, filed on Aug. 25, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,394 bytes ASCII (Text) file named "722862SequenceListing.txt," created Dec. 23, 2015.

TECHNICAL FIELD

The present invention relates to a glycoside compound, a production method of thioether, ether, a production method of ether, a production method of glycoside compound, and a production method of nucleic acid.

BACKGROUND ART

As a production (synthesis) method of nucleic acids such as DNA, RNA and the like, for example, a phosphoramidite method and the like are used. As a starting material for the nucleic acid synthesis by the phosphoramidite method, phosphoramidite of nucleoside (hereinafter to be simply referred to as "phosphoramidite") is used. Examples of the protecting group at the 2'-position of the aforementioned phosphoramidite include many protecting groups such as TBDMS (tert-butyldimethylsilyl) group, TOM (triisopropylsilyloxymethyl) group, ACE (bis(2-acetoxyethoxy) methyl) group and the like. As for TOM amidite, it is described in, for example, the following non-patent document 1 and the like.

DOCUMENT LIST

Non-patent Document

Non-patent Document 1:
http://www.glenresearch.com/Technical/TB_RNA_TOM_Deprotection.pdf (searched on Aug. 18, 2011)

SUMMARY OF THE INVENTION

Problems to be Solved by the Invention

However, since the production cost of conventional phosphoramidites such as TOM amidite, ACE amidite and the like is high, they are not convenient as starting materials for the synthesis of pharmaceutical products and the like. In addition, the yield and purity of nucleic acid are sometimes not very high when nucleic acid is synthesized by a coupling (condensation) reaction using TBDMS amidite.

Therefore, the present invention aims to provide a glycoside compound, a production method of thioether, ether, a production method of ether, and a production method of a glycoside compound, which are capable of providing a phosphoramidite which can be produced at a low cost and can produce a nucleic acid in a high yield and with high purity. Furthermore, the present invention aims to provide a production method of a nucleic acid, which can produce a nucleic acid in a high yield and with high purity by using the aforementioned phosphoramidite.

Means of Solving the Problems

To achieve the aforementioned object, the glycoside compound of the present invention is
a glycoside compound represented by the following chemical formula (1), an enantiomer thereof, a tautomer or stereoisomer thereof or a salt thereof:

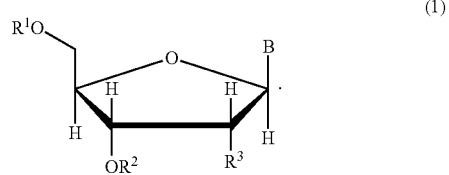
(1)

In the aforementioned chemical formula (1),
B is an atomic group having a nucleic acid base skeleton, and optionally having a protecting group,
$R^1$ and $R^2$ are each a hydrogen atom or a protecting group,
or $R^1$ and $R^2$ in conjunction optionally form an atomic group represented by the following chemical formula ($R^1R^2A$) or ($R^1R^2B$):

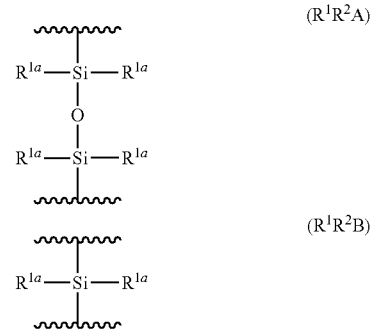

each $R^{1a}$ is a hydrogen atom, a straight chain or branched alkyl group, or a straight chain or branched alkoxy group, which may be the same or different,
$R^3$ is a group represented by the following chemical formula ($R^3$):

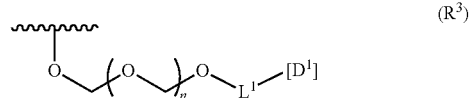
($R^3$)

in the aforementioned chemical formula ($R^3$),
$L^1$ is an ethylene group (—CH$_2$CH$_2$—), wherein hydrogen atoms besides a hydrogen atom bonded to the α-position relative to [$D^1$] are optionally substituted by a straight chain or branched alkyl group,
n is a positive integer, and
[$D^1$] is an electron-withdrawing group.

The first production method of thioether in the present invention includes a coupling reaction of thiol or thioalkoxide represented by the following chemical formulas (101a) and (101b) with a halide represented by the following chemical formula (102) to give a thioether represented by the following chemical formula (103).

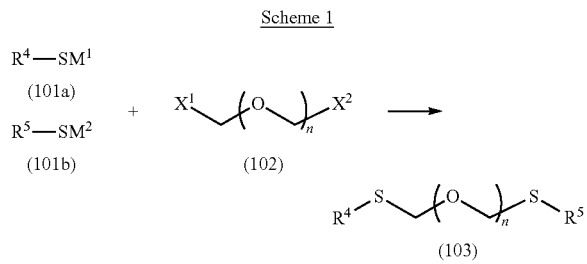

Scheme 1

In the aforementioned chemical formulas (101a), (101b) and (103), $R^4$ and $R^5$ are each a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same or different, in the aforementioned chemical formulas (101a) and (101b), $M^1$ and $M^2$ may be the same or different and each is a hydrogen atom or a metal, in the aforementioned chemical formulas (102) and (103), n is a positive integer, and in the aforementioned chemical formula (102), $X^1$ and $X^2$ may be the same or different and each is halogen.

The second production method of thioether in the present invention includes a coupling reaction of a thioether represented by the following chemical formula (103b) and an alcohol represented by the following chemical formula (104), in the presence of a halogenating agent and a Lewis acid to give a thioether represented by the following chemical formula (103).

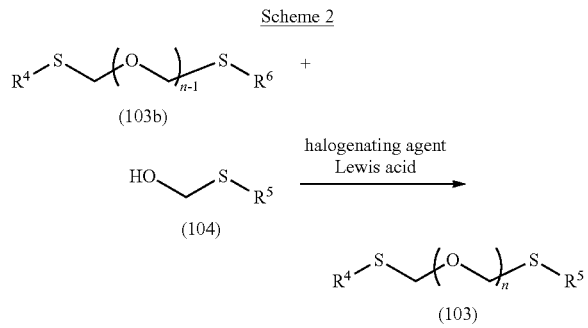

Scheme 2

In the aforementioned chemical formulas (103b), (104) and (103), $R^4$, $R^5$ and $R^6$ are each a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same or different, and in the aforementioned chemical formulas (103b) and (103), n is an integer of two or more.

The ether in the present invention is an ether represented by the following chemical formula (106), an enantiomer thereof, a tautomer or stereoisomer thereof or a salt thereof.

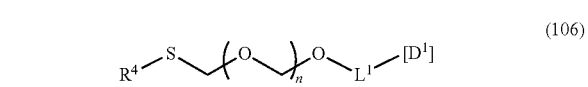

In the aforementioned chemical formula (106), $R^4$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, n is a positive integer, $L^1$ is an ethylene group ($-CH_2CH_2-$), wherein hydrogen atoms besides a hydrogen atom bonded to the α-position relative to $[D^1]$ are optionally substituted by a straight chain or branched alkyl group, and $[D^1]$ is an electron-withdrawing group.

The production method of the ether in the present invention includes a coupling reaction of a thioether represented by the following chemical formula (103) and an alcohol represented by the following chemical formula (105), in the presence of a halogenating agent and a Lewis acid to give the aforementioned ether in the present invention.

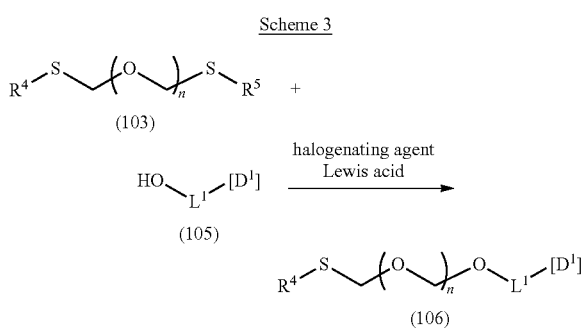

Scheme 3

In the aforementioned chemical formulas (103) and (105), $R^4$ is as defined for the aforementioned chemical formula (106), $R^5$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same as or different from $R^4$, in the aforementioned chemical formula (103),
n is as defined for the aforementioned chemical formula (106), and in the aforementioned chemical formula (105),
$L^1$ and $[D^1]$ are as defined for the aforementioned chemical formula (106).

The production method of the glycoside compound in the present invention is a production method of the aforementioned glycoside compound of the present invention, an enantiomer thereof, a tautomer or stereoisomer thereof or a salt thereof, which includes a coupling step including a coupling reaction of a glycoside compound represented by the following chemical formula (107) and an ether represented by the following chemical formula (106), in the presence of a halogenating agent and a Lewis acid to give a glycoside compound represented by the following chemical formula (1a), wherein the glycoside compound represented by the following chemical formula (1a) is the glycoside compound which is a glycoside compound wherein $R^1$ and $R^2$ in the aforementioned chemical formula (1) in conjunction form an atomic group represented by the aforementioned chemical formula ($R^1R^2A$) or ($R^1R^2B$).

Scheme 4

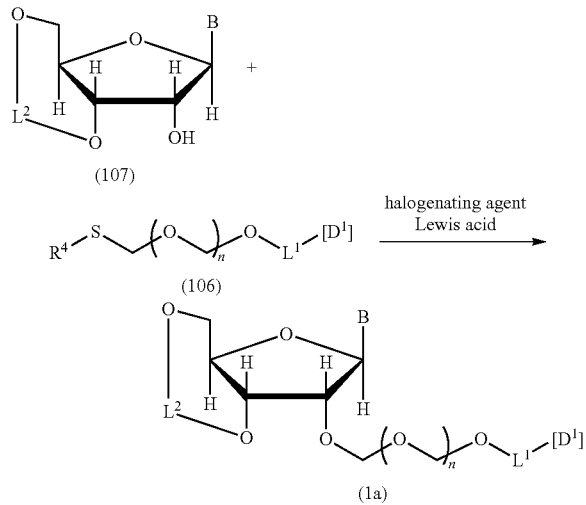

In the aforementioned chemical formulas (107) and (1a),
$L^2$ is an atomic group represented by the aforementioned chemical formula ($R^1R^2A$) or ($R^1R^2B$),
B is as defined for the aforementioned chemical formula (1),
in the aforementioned chemical formula (106),
$R^4$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, and in the aforementioned chemical formulas (106) and (1a), $L^1$, n and $[D^1]$ are as defined for the aforementioned chemical formula (1).

The production method of a nucleic acid in the present invention is a production method of a nucleic acid having the structure represented by the following chemical formula (I), and is characterized by including a condensation step for condensing the glycoside compound of the present invention wherein the glycoside compound represented by the aforementioned chemical formula (1) is the glycoside compound represented by the aforementioned chemical formula (2).

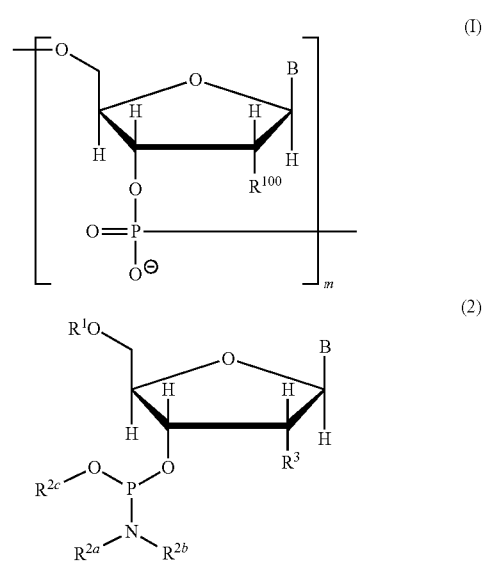

In the aforementioned chemical formula (I), B is as defined for the aforementioned chemical formula (1),
$R^{100}$ is a hydrogen atom or a hydroxyl group,
respective B may be the same or different, and respective $R^{100}$ may be the same or different,
m is a positive integer.

In the aforementioned chemical formula (2),
B, $R^1$ and $R^3$ are as defined for the aforementioned chemical formula (1),
provided that $R^1$ is a protecting group,
$R^{2a}$ and $R^{2b}$ may be the same or different and each is a hydrogen atom or any substituent,
or $R^{2a}$ and $R^{2b}$ optionally form a nonaromatic ring, in conjunction with a nitrogen atom to which they are bonded, the aforementioned nonaromatic ring optionally has a nitrogen atom, an oxygen atom or a sulfur atom, besides the aforementioned nitrogen atom, and optionally has a substituent, and
$R^{2c}$ is a hydrogen atom, an electron-withdrawing group or any substituent, which may be optionally substituted by an electron-withdrawing group $[D^2]$.

Effect of the Invention

According to the glycoside compound, the production method of thioether, ether, the production method of ether, and the production method of a glycoside compound, of the present invention, phosphoramidite that can be produced at a low cost and can produce a nucleic acid in a high yield and with high purity can be provided. Moreover, according to the production method of a nucleic acid in the present invention, a nucleic acid can be produced in a high yield and with high purity by using the aforementioned phosphoramidite.

DESCRIPTION OF EMBODIMENTS

Figure 1:
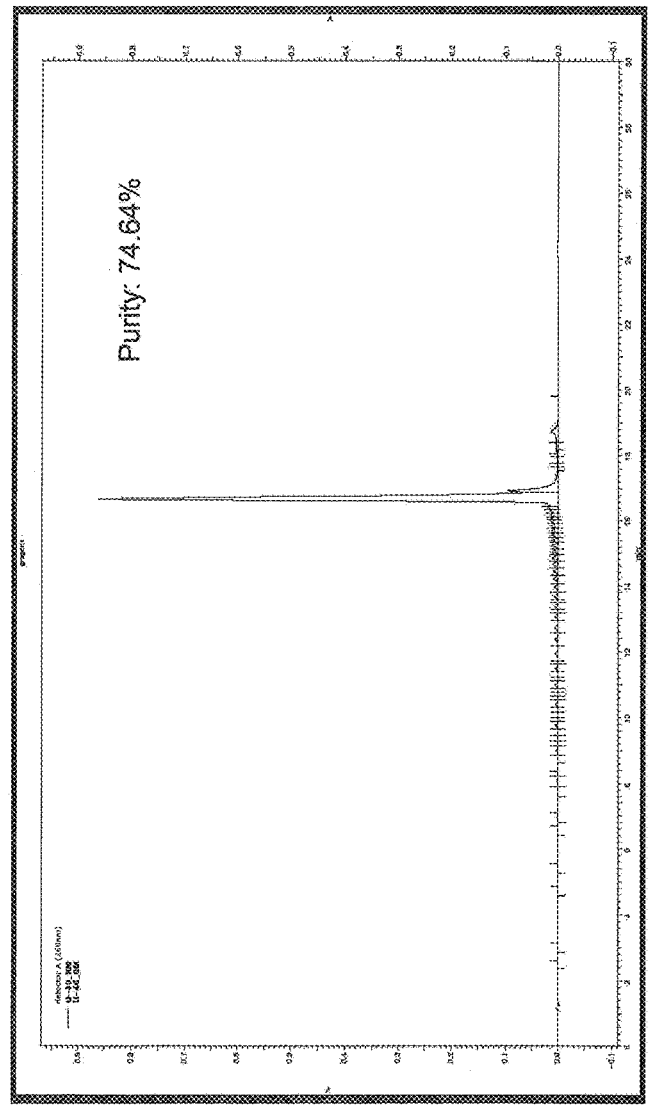
FIG. 1 is an HPLC chart of the nucleic acid (before purification) produced in Example 6.

The present invention is explained in detail by way of Examples. However, the present invention is not limited by the following explanation.

Unless particularly specified, the terms used in the present specification can be used in the meanings generally adopted in the pertinent technical field.

According to the present invention, for example, one or more effects from the following [1]-[5] can be obtained. However, these effects are exemplary and do not limit the present invention.

[1] Of the glycoside compounds represented by the aforementioned chemical formula (1) of the present invention, a glycoside compound represented by the aforementioned chemical formula (2) (phosphoramidite) can be preferably used as a starting material for the synthesis of nucleic acid. In the glycoside compound represented by the aforementioned chemical formula (2) (phosphoramidite), an electron-withdrawing group [$D^1$] is farther from phosphate group than TOM amidite, ACE amidite and the like and the interaction between [$D^1$] and the phosphate group is weak. Therefore, glycoside compound (2) is more easily synthesized than conventional amidites such as TOM amidite, ACE amidite and the like and can be obtained with high purity.

[2] Since the glycoside compound of the present invention can be produced at a lower cost than conventional ACE amidite, TOM amidite and the like, it is suitable as a starting material of medicaments and the like.

[3] The thioether represented by the aforementioned chemical formula (103) and the ether represented by the aforementioned chemical formula (106), which are the synthesis intermediates for the glycoside compound of the present invention, can be produced at a low cost, by producing according to the aforementioned production method of the present invention. Consequently, the glycoside compound of the present invention can be produced at a still lower cost.

[4] Particularly, the thioether represented by the aforementioned chemical formula (103) is useful as a synthesis intermediate for pharmaceutical products, which is not only for the glycoside compound of the present invention. According to the aforementioned first and second production methods of thioether in the present invention, the thioether represented by the aforementioned chemical formula (103) can be synthesized in a higher yield and at a lower cost than in the past.

[5] The production method of a nucleic acid in the present invention can produce a nucleic acid with high purity and in a high yield by using the glycoside compound represented by the aforementioned chemical formula (2) (phosphoramidite) in the present invention. Specifically, for example, it is also possible to synthesize RNA at a purity comparable to that in DNA synthesis. While the reason therefor is not clear, for example, improved efficiency of condensation reaction (coupling reaction) due to less steric hindrance during condensation reaction (coupling reaction) as compared to ACE amidite, TOM amidite and the like, and the like are considered. In addition, the glycoside compound represented by the aforementioned chemical formula (2) in the present invention permits easy deprotection in the condensation reaction (coupling reaction).

1. Glycoside Compound

The glycoside compound of the present invention is, as mentioned above, a glycoside compound represented by the following chemical formula (1), an enantiomer thereof, a tautomer or stereoisomer thereof or a salt thereof:

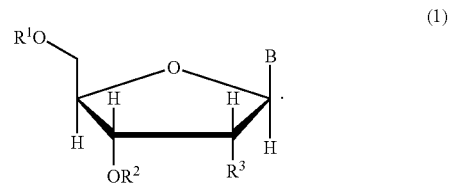

(1)

In the aforementioned chemical formula (1),

B is an atomic group having a nucleic acid base skeleton, and optionally having a protecting group, $R^1$ and $R^2$ are each a hydrogen atom or a protecting group, or $R^1$ and $R^2$ in conjunction optionally form an atomic group represented by the following chemical formula ($R^1R^2A$) or ($R^1R^2B$):

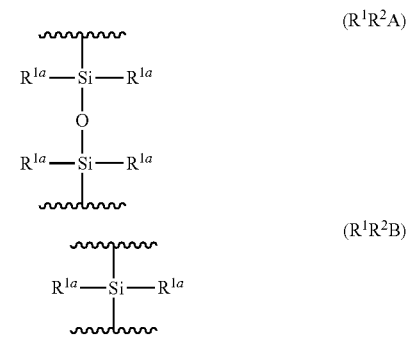

each $R^{1a}$ is a hydrogen atom, a straight chain or branched alkyl group, or a straight chain or branched alkoxy group, which may be the same or different, $R^3$ is a group represented by the following chemical formula ($R^3$):

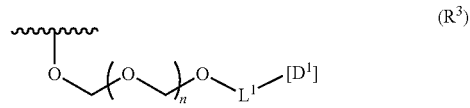

in the aforementioned chemical formula ($R^3$), $L^1$ is an ethylene group (—$CH_2CH_2$—), wherein hydrogen atoms besides a hydrogen atom bonded to the α-position relative to [$D^1$] are optionally substituted by a straight chain or branched alkyl group, n is a positive integer, and

[$D^1$] is an electron-withdrawing group. Note that "bonded to the α-position relative to [$D^1$]" means being bonded to the same carbon atom to which [$D^1$] is bonded.

As the electron-withdrawing group [$D^1$] in the aforementioned chemical formula (1), a cyano group, a nitro group, an alkylsulfonyl group, halogen, an arylsulfonyl group, a trihalomethyl group, or a trialkylamino group is preferable. The aforementioned trihalomethyl group is, for example, a trichloromethyl group, a trifluoromethyl group or the like. In the aforementioned chemical formula (1), the aforementioned straight chain or branched alkyl group for $L^1$ may be, for example, a straight chain or branched alkyl group having 1-12 carbon atoms. $L^1$ is particularly preferably an unsubstituted ethylene group (—$CH_2CH_2$—). In the aforementioned chemical formula (1), n is not particularly limited and, for example, within the range of 1-30, preferably 1-20.

In the aforementioned chemical formula (1), $R^1$ is, as mentioned above, a hydrogen atom or a protecting group. The protecting group $R^1$ is not particularly limited and is, for example, a substituent represented by any of the following chemical formulas ($R^1A$), ($R^1B$), ($R^1C$) and ($R^1D$).

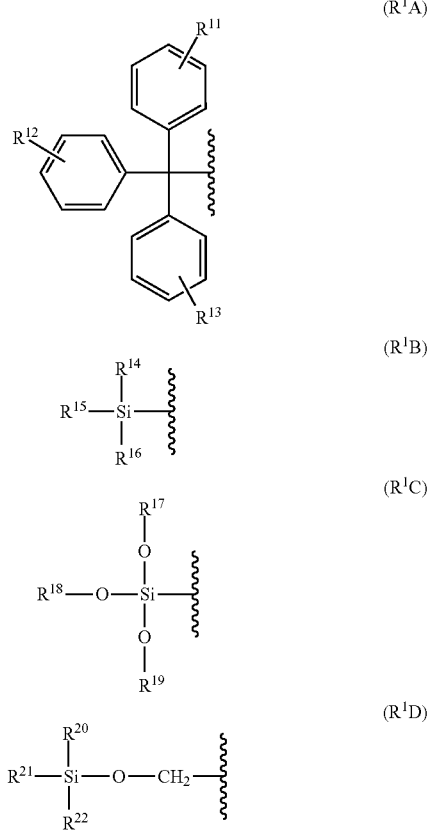

In the aforementioned chemical formula ($R^1A$), $R^{11}$-$R^{13}$ may be the same or different and each is a straight chain or branched alkoxy group, or a straight chain or branched alkyl group, or absent, $R^{11}$-$R^{13}$ are, when they are present, respectively present singly or in plurality, and when present in plurality, they may be the same or different, in the aforementioned chemical formula ($R^1B$), $R^{14}$-$R^{16}$ may be the same or different and each is a hydrogen atom, a straight chain or branched alkyl group, or a straight chain or branched alkoxy group, in the aforementioned chemical formula ($R^1C$), $R^{17}$-$R^{19}$ are each a hydrogen atom, halogen, a hydrocarbon group, a straight chain or branched alkyl group, a straight chain or branched alkenyl group, a straight chain or branched alkynyl group, a straight chain or branched haloalkyl group, an aryl group, a heteroaryl group, a straight chain or branched arylalkyl group, a cycloalkyl group, a cycloalkenyl group, a straight chain or branched cycloalkylalkyl group, a straight chain or branched cyclylalkyl group, a straight chain or branched hydroxyalkyl group, a straight chain or branched alkoxyalkyl group, a straight chain or branched aminoalkyl group, a straight chain or branched heterocyclylalkenyl group, a straight chain or branched heterocyclylalkyl group, a straight chain or branched heteroarylalkyl group, a silyl group, a silyloxyalkyl group, a mono-, di- or trialkylsilyl group, or a mono-, di- or trialkylsilyloxyalkyl group, which may be the same or different, in the aforementioned chemical formula ($R^1D$), $R^{20}$-$R^{22}$ may be the same or different and each is a hydrogen atom, or a straight chain or branched alkyl group.

In the aforementioned chemical formula ($R^1A$), preferably, $R^{11}$-$R^{13}$ may be the same or different and each is a straight chain or branched alkoxy group having 1-12 carbon atoms, or a straight chain or branched alkyl group having 1-12 carbon atoms, or absent. As mentioned above, $R^{11}$-$R^{13}$ are, when they are present, respectively present singly or in plurality, and when present in plurality, they may be the same or different. In the aforementioned chemical formula ($R^1B$), preferably, $R^{14}$-$R^{16}$ may be the same or different and each is a hydrogen atom, a straight chain or branched alkyl group having 1-12 carbon atoms, or a straight chain or branched alkoxy group having 1-12 carbon atoms. In the aforementioned chemical formula ($R^1C$), preferably, $R^{17}$-$R^{19}$ are each a hydrogen atom, halogen, a straight chain or branched alkyl group having 1-12 carbon atoms, a straight chain or branched alkenyl group having 2-12 carbon atoms, a straight chain or branched alkynyl group having 2-12 carbon atoms, a straight chain or branched haloalkyl group having 1-12 carbon atoms, an aryl group having 5-24 carbon atoms, a heteroaryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, a straight chain or branched hydroxyalkyl group having 1-12 carbon atoms, a straight chain or branched alkoxyalkyl group having 1-12 carbon atoms, a straight chain or branched aminoalkyl group having 1-12 carbon atoms, a straight chain or branched heterocyclylalkenyl group having 5-30 carbon atoms, a straight chain or branched heterocyclylalkyl group having 4-30 carbon atoms, a straight chain or branched heteroarylalkyl group having 6-30 carbon atoms, a silyl group, a silyloxyalkyl group having 1-12 carbon atoms, a mono-, di- or trialkylsilyl group having alkyl carbon number 1-12, or an alkyl group having 1-12 carbon atoms and substituted by a mono-, di- or trialkylsilyloxy group having alkyl carbon number 1-12, which may be the same or different. In the aforementioned chemical formula ($R^1D$), preferably, $R^{20}$-$R^{22}$ may be the same or different and each is a hydrogen atom, or a straight chain or branched alkyl group having 1-12 carbon atoms.

In the glycoside compound of the present invention, the substituent represented by the aforementioned chemical formula ($R^1A$) is preferably a substituent represented by the following chemical formula ($R^2A^2$).

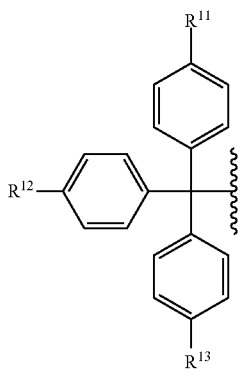

(R¹A2)

In the aforementioned chemical formula (R¹A²), $R^{11}$-$R^{13}$ may be the same or different and each is a hydrogen atom, a straight chain or branched alkoxy group, or a straight chain or branched alkyl group.

In the aforementioned chemical formula (R¹A²), more preferably, $R^{11}$-$R^{13}$ may be the same or different and each is a hydrogen atom, a straight chain or branched alkoxy group having 1-12 carbon atoms, or a straight chain or branched alkyl group having 1-12 carbon atoms.

In the glycoside compound of the present invention, $R^1$ in the aforementioned chemical formula (1) is more preferably a hydrogen atom, or a substituent represented by the following chemical formula (R¹Aa), (R¹Ba), (R¹Ca), (R¹Cb) or (R¹Da).

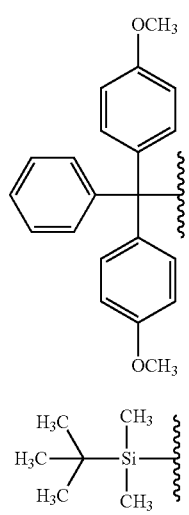

(R¹Aa)

(R¹Ba)

(R¹Ca)

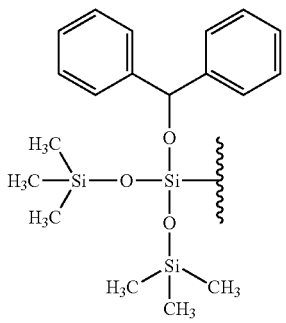

(R¹Cb)

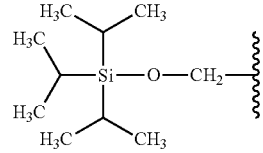

(R¹Da)

In the aforementioned chemical formulas (R¹R²A) and (R¹R²B) in the glycoside compound of the present invention, respective $R^{1a}$ may be the same or different, as mentioned above, and each is a hydrogen atom, a straight chain or branched alkyl group, or a straight chain or branched alkoxy group. The aforementioned straight chain or branched alkyl group is more preferably a straight chain or branched alkyl group having 1-12 carbon atoms. The aforementioned straight chain or branched alkoxy group is more preferably a straight chain or branched alkoxy group having 1-12 carbon atoms.

In the glycoside compound of the present invention, the glycoside compound represented by the aforementioned chemical formula (1) is preferably the glycoside compound represented by the aforementioned chemical formula (2).

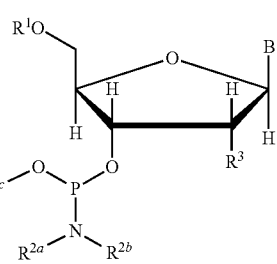

(2)

In the aforementioned chemical formula (2),

B, $R^1$ and $R^3$ are as defined for the aforementioned chemical formula (1), provided that $R^1$ is a protecting group, $R^{2a}$ and $R^{2b}$ may be the same or different and each is a hydrogen atom or any substituent, or $R^{2a}$ and $R^{2b}$ optionally form a nonaromatic ring, in conjunction with a nitrogen atom to which they are bonded, the aforementioned nonaromatic ring optionally has a nitrogen atom, an oxygen atom or a sulfur atom, besides the aforementioned nitrogen atom, and optionally has a substituent, and $R^{2c}$ is a hydrogen atom, an electron-withdrawing group or any substituent, which may be optionally substituted by an electron-withdrawing group [D²].

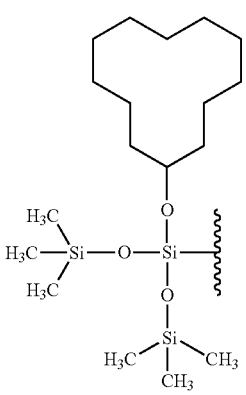

In the aforementioned chemical formula (2), $R^{2a}$ and $R^{2b}$ are each a hydrogen atom, halogen, a hydrocarbon group, a straight chain or branched alkyl group, a straight chain or branched alkenyl group, a straight chain or branched alkynyl group, a straight chain or branched haloalkyl group, an aryl group, a heteroaryl group, a straight chain or branched arylalkyl group, a cycloalkyl group, a cycloalkenyl group, a straight chain or branched cycloalkylalkyl group, a straight chain or branched cyclylalkyl group, a straight chain or branched hydroxyalkyl group, a straight chain or branched alkoxyalkyl group, a straight chain or branched aminoalkyl group, a straight chain or branched heterocyclylalkenyl group, a straight chain or branched heterocyclylalkyl group, a straight chain or branched heteroarylalkyl group, a silyl group, a silyloxyalkyl group, a mono-, di- or trialkylsilyl group, or a mono-, di- or trialkylsilyloxyalkyl group, which is preferably optionally further substituted or not substituted by an electron-withdrawing group. Alternatively, $R^{2a}$ and $R^{2b}$ may form, in conjunction with the nitrogen atom bonded thereto, a 5- or 6-membered nonaromatic ring, wherein the aforementioned nonaromatic ring may or may not have a nitrogen atom, an oxygen atom or a sulfur atom besides the aforementioned nitrogen atom, and may or may not further have a substituent.

In the aforementioned chemical formula (2), more preferably, $R^{2a}$ and $R^{2b}$ are each a hydrogen atom, halogen, a straight chain or branched alkyl group having 1-12 carbon atoms, a straight chain or branched alkenyl group having 2-12 carbon atoms, a straight chain or branched alkynyl group having 2-12 carbon atoms, a straight chain or branched haloalkyl group having 1-12 carbon atoms, an aryl group having 5-24 carbon atoms, a heteroaryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, a straight chain or branched hydroxyalkyl group having 1-12 carbon atoms, a straight chain or branched alkoxyalkyl group having 2-12 carbon atoms, a straight chain or branched aminoalkyl group having 1-12 carbon atoms, a straight chain or branched heterocyclylalkenyl group having 5-30 carbon atoms, a straight chain or branched heterocyclylalkyl group having 4-30 carbon atoms, a straight chain or branched heteroarylalkyl group having 6-30 carbon atoms, a silyl group, a silyloxyalkyl group having 1-12 carbon atoms, a mono-, di- or trialkylsilyl group having alkyl carbon number 1-12, or an alkyl group having 1-12 carbon atoms and substituted by a mono-, di- or trialkylsilyloxy group having alkyl carbon number 1-12, which may be further substituted or not substituted by an electron-withdrawing group. Alternatively, $R^{2a}$ and $R^{2b}$ may form, in conjunction with the nitrogen atom bonded thereto, a 5- or 6-membered nonaromatic ring. The aforementioned nonaromatic ring may or may not have a nitrogen atom, an oxygen atom or a sulfur atom besides the aforementioned nitrogen atom, and may or may not further have a substituent.

In the aforementioned chemical formula (2), more preferably, $R^{2a}$ and $R^{2b}$ are each a methyl group, an ethyl group, an isopropyl group, or a t-butyl group, or $R^{2a}$ and $R^{2b}$ form, in conjunction with a nitrogen atom bonded thereto, a piperidyl group, a morpholino group, a pyrrolidyl group, a thiomorpholino group, or other nitrogen-containing alicyclic group. More specifically, for example, in the aforementioned chemical formula (2), —$NR^{2a}R^{2b}$ is more preferably a diisopropylamino group, a diethylamino group, an ethylmethylamino group, a pyrrolidyl (particularly, pyrrolidin-1-yl) group, a piperidyl (particularly, piperidin-1-yl) group, a morpholino (particularly, morpholin-1-yl) group, a thiomorpholino (particularly, thiomorpholin-1-yl) group, or an arylamino group.

In the aforementioned chemical formula (2), $R^{2c}$ is a hydrogen atom, halogen, a hydrocarbon group, a straight chain or branched alkyl group, a straight chain or branched alkenyl group, a straight chain or branched alkynyl group, a straight chain or branched haloalkyl group, an aryl group, a heteroaryl group, a straight chain or branched arylalkyl group, a cycloalkyl group, a cycloalkenyl group, a straight chain or branched cycloalkylalkyl group, a straight chain or branched cyclylalkyl group, a straight chain or branched hydroxyalkyl group, a straight chain or branched alkoxyalkyl group, a straight chain or branched aminoalkyl group, a straight chain or branched heterocyclylalkenyl group, a straight chain or branched heterocyclylalkyl group, a straight chain or branched heteroarylalkyl group, a silyl group, a silyloxyalkyl group, a mono-, di- or trialkylsilyl group, or a mono-, di- or trialkylsilyloxyalkyl group, and further preferably may or may not be substituted by an electron-withdrawing group [$D^2$].

In the aforementioned chemical formula (2), $R^{2c}$ is a hydrogen atom, halogen, a straight chain or branched alkyl group having 1-12 carbon atoms, a straight chain or branched alkenyl group having 2-12 carbon atoms, a straight chain or branched alkynyl group having 2-12 carbon atoms, a straight chain or branched haloalkyl group having 1-12 carbon atoms, an aryl group having 5-24 carbon atoms, a heteroaryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, a straight chain or branched hydroxyalkyl group having 1-12 carbon atoms, a straight chain or branched alkoxyalkyl group having 2-12 carbon atoms, a straight chain or branched aminoalkyl group having 1-12 carbon atoms, a straight chain or branched heterocyclylalkenyl group having 6-30 carbon atoms, a straight chain or branched heterocyclylalkyl group having 4-30 carbon atoms, a straight chain or branched heteroarylalkyl group having 6-30 carbon atoms, a silyl group, a silyloxyalkyl group having 1-12 carbon atoms, a mono-, di- or trialkylsilyl group having alkyl carbon number 1-12, or an alkyl group having 1-12 carbon atoms and substituted by a mono-, di- or trialkylsilyloxy group having alkyl carbon number 1-12, and more preferably may or may not be further substituted by an electron-withdrawing group [$D^2$].

In the aforementioned chemical formula (2), $R^{2c}$ is more preferably a straight chain or branched alkyl group substituted by an electron-withdrawing group [$D^2$]. In the aforementioned chemical formula (2), $R^{2c}$ is more preferably a straight chain or branched alkyl group having 1-12 carbon atoms and substituted by an electron-withdrawing group [$D^2$].

In the aforementioned chemical formula (2), the aforementioned electron-withdrawing group [$D^2$] for $R^{2c}$ is preferably a cyano group, a nitro group, an alkylsulfonyl group, halogen, an arylsulfonyl group, a trihalomethyl group, or a trialkylamino group. The aforementioned trihalomethyl group is, for example, a trichloromethyl group, a trifluoromethyl group or the like.

In the aforementioned chemical formula (2), $R^{2c}$ is particularly preferably an alkenyl group or an ethynyl group, or substituted by an electron-withdrawing group [$D^2$] and form, together with [$D^2$], a cyanoethyl group.

In the glycoside compound of the present invention, the glycoside compound represented by the aforementioned chemical formula (1) is more preferably a glycoside compound represented by the following chemical formula (3).

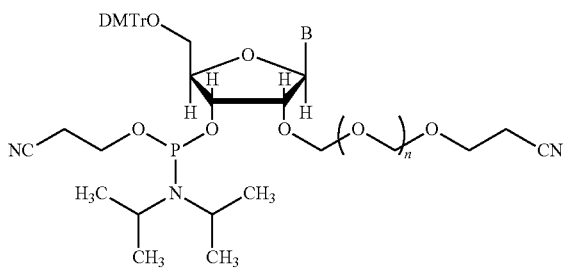

(3)

In the aforementioned chemical formula (3),

B and n are as defined for the aforementioned chemical formula (1), and

DMTr is a 4,4'-dimethoxy(triphenylmethyl) group.

In the glycoside compound of the present invention, the nucleic acid base for B in the aforementioned chemical formula (1) is not particularly limited, but is preferably an atomic group having a natural nucleic acid base skeleton. The aforementioned natural nucleic acid base may or may not have a protecting group. The aforementioned natural nucleic acid base is more preferably adenine, cytosine, guanine, uracil, thymine, or other nitrogen-containing aromatic ring. In the aforementioned chemical formula (1), B is more preferably bonded to the D-ribose skeleton in the aforementioned chemical formula (1) at the 9-position nitrogen of adenine, the 1-position nitrogen of cytosine, 9-position nitrogen of guanine, the 1-position nitrogen of uracil or the 1-position nitrogen of thymine. In addition, as for the nucleic acid base for B, the nucleic acid base (e.g., the aforementioned nucleic acid bases such as adenine, cytosine, guanine, uracil, thymine and the like) may be substituted or not substituted by any substituent. Examples of the aforementioned substituent include halogen, an acyl group, an alkyl group, an arylalkyl group, an alkoxy group, an alkoxyalkyl group, a hydroxy group, an amino group, a monoalkylamino group, a dialkylamino group, a carboxy group, a cyano group, a nitro group and the like. These substituents may be 0, 1 or plural (for example, 2-3). When they are in plurality, the kind thereof may be one or plural.

As mentioned above, B may or may not have a protecting group. For example, when the aforementioned nucleic acid base for B has an amino group (amino substituent) outside the ring (e.g., the aforementioned nucleic acid base is adenine, guanine, cytosine etc.), the aforementioned amino group may be protected by a protecting group. The aforementioned amino-protecting group is not particularly limited and, for example, may be the same as the protecting group etc. used in known nucleic acids chemistry. Examples of the aforementioned amino-protecting group include acyl group. Examples of the aforementioned acyl group include benzoyl group, 4-methoxybenzoyl group, acetyl group, propionyl group, butyryl group, isobutyryl group, phenylacetyl group, phenoxyacetyl group, 4-tert-butylphenoxyacetyl group, 4-isopropylphenoxyacetyl group and the like. Other than acyl group, for example, a (dimethylamino)methylene group and the like.

In the glycoside compound of the present invention, the glycoside compound represented by the aforementioned chemical formula (1) is more preferably a glycoside compound represented by the following chemical formula ($1A^{Ac}$), ($1C^{Ac}$), ($1 G^{Pac}$) or (1U).

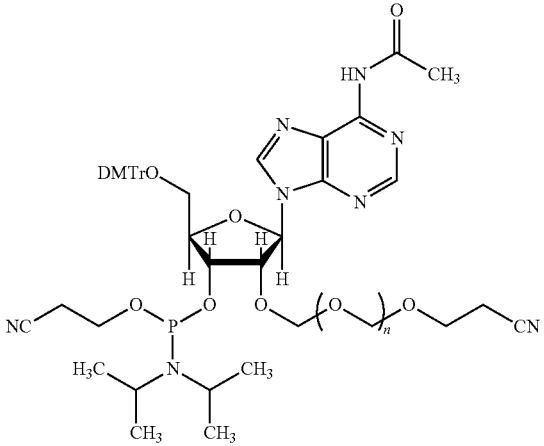

($1A^{Ac}$)

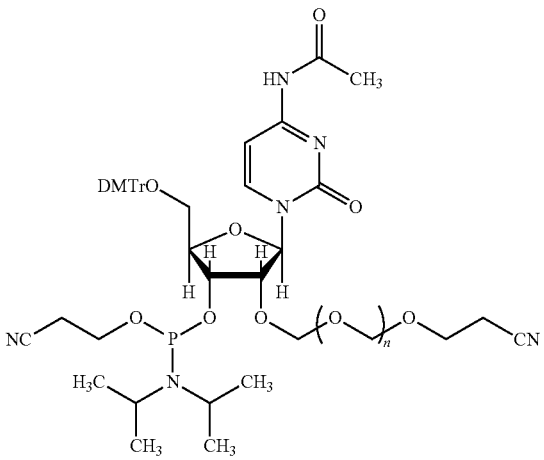

($1C^{Ac}$)

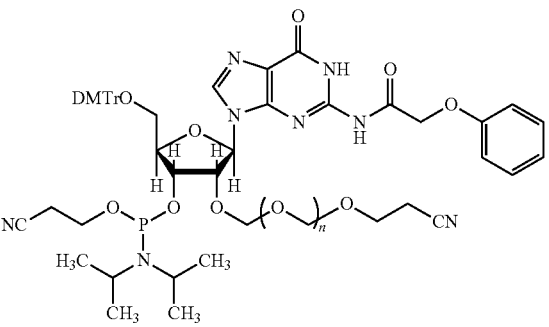

($1G^{Pac}$)

-continued (1U)

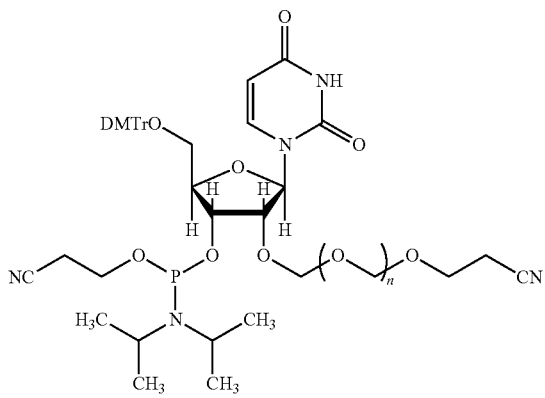

In the aforementioned chemical formulas (1A$^{Ac}$), (1C$^{Ac}$), (1 G$^{Pac}$) and (1U), n are as defined for the aforementioned chemical formula (1).

In the aforementioned chemical formula (1), n=1 is particularly preferable from the aspects of easiness of synthesis and the like.

When an isomer such as enantiomer, tautomer or stereoisomer (e.g., geometric isomer, conformational isomer and optical isomer) and the like is present in the novel compounds provided by the present invention such as the glycoside compound, ether and the like of the present invention (hereinafter sometimes to be simply referred to as "the compound of the present invention"), all isomers are encompassed in the compound of the present invention. For example, while the chemical formulas showing the glycoside compounds of the present invention (the aforementioned chemical formulas (1), (2) and (3) etc.) depicts as if the sugar skeleton of glycoside is D-ribose, it may be an enantiomer thereof, i.e., L-ribose. When the compound of the present invention can form a salt, such salt is also encompassed in the compound of the present invention. The aforementioned salt of the compound of the present invention may be an acid addition salt or a base addition salt. Furthermore, an acid that forms the aforementioned acid addition salt may be an inorganic acid or an organic acid, and a base that forms the aforementioned base addition salt may be an inorganic base or an organic base. While the aforementioned inorganic acid is not particularly limited, for example, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chlorine acid, bromine acid, iodine acid, perfluoric acid, perchloric acid, perbromic acid, periodic acid and the like can be mentioned. While the aforementioned organic acid is not particularly limited, for example, p-toluenesulfonic acid, methanesulfonic acid, oxalic acid, p-bromobenzenesulfonic acid, carbonic acid, succinic acid, citric acid, benzoic acid, acetic acid and the like can be mentioned. While the aforementioned inorganic base is not particularly limited, for example, ammonium hydroxide, alkali metal hydroxide, alkaline earth metal hydroxide, carbonate and hydrogencarbonates and the like can be mentioned and, more specifically, for example, sodium hydroxide, potassium hydroxide, potassium carbonate, sodium carbonate, sodium hydrogen carbonate, potassium hydrogen carbonate, calcium hydroxide and calcium carbonate and the like can be mentioned. The aforementioned organic base is not particularly limited and, for example, ethanolamine, triethylamine and tris(hydroxymethyl)aminomethane and the like can be mentioned. The production method of these salts is not particularly limited, and they can be produced by, for example, a method including appropriately adding the aforementioned acid or base to the aforementioned electron donor acceptor connected molecule by a known method and the like. When an isomer is present in the substituent and the like, any isomer can be used. For example, the "naphthyl group" may be a 1-naphthyl group or a 2-naphthyl group, and the "propyl group" may be an n-propyl group or an isopropyl group.

In the present invention, "alkyl" includes, for example, linear or branched alkyl. The carbon number of the aforementioned alkyl is not particularly limited and, for example, 1-30, preferably 1-12, 1-6 or 1-4. Examples of the aforementioned alkyl include methyl, ethyl, n-propyl, isopropyl, n-butyl, isobutyl, sec-butyl and tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like. Preferably, for example, methyl, ethyl, n-propyl, isopropyl, n-butyl, isobutyl, sec-butyl, tert-butyl, n-pentyl, isopentyl, neopentyl, n-hexyl, isohexyl and the like can be mentioned. The same applies to a group containing an alkyl group in the structure (alkylamino group, alkoxy group etc.), and a group induced from an alkyl group (haloalkyl group, hydroxyalkyl group, aminoalkyl group, alkanoyl group etc.).

In the present invention, "alkenyl" includes, for example, linear or branched alkenyl. The aforementioned alkenyl is, for example, the aforementioned alkyl containing one or plural double bonds and the like. The carbon number of the aforementioned alkenyl is not particularly limited and, for example, the same as for the aforementioned alkyl and preferably 2-12 or 2-8. Examples of the aforementioned alkenyl include vinyl, 1-propenyl, 2-propenyl, 1-butenyl, 2-butenyl, 3-butenyl, 1,3-butadienyl, 3-methyl-2-butenyl and the like.

In the present invention, "alkynyl" includes, for example, linear or branched alkynyl. The aforementioned alkynyl is, for example, the aforementioned alkyl containing one or plural triple bonds and the like. The carbon number of the aforementioned alkynyl is not particularly limited and, for example, the same as for the aforementioned alkyl and preferably 2-12 or 2-8. Examples of the aforementioned alkynyl include ethynyl, propynyl, butynyl and the like. The aforementioned alkynyl may further have, for example, one or plural double bonds.

In the present invention, "aryl" includes, for example, a monocyclic aromatic hydrocarbon group and a polycyclic aromatic hydrocarbon group. Examples of the aforementioned monocyclic aromatic hydrocarbon group include phenyl and the like. Examples of the aforementioned polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like. Preferably, for example, phenyl, naphthyl such as 1-naphthyl and 2-naphthyl and the like, and the like can be mentioned.

In the present invention, "heteroaryl" includes, for example, a monocyclic aromatic heterocyclic group and a fused aromatic heterocyclic group. Examples of the aforementioned heteroaryl include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, -benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, benzothiazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl) and the like.

In the present invention, "cycloalkyl" is, for example, a cyclic saturated hydrocarbon group, and the carbon number is not particularly limited and is, for example, 3-24 or 3-15. Examples of the aforementioned cycloalkyl include cyclopropyl, cyclobutyl, cyclopentyl, cyclohexyl, cycloheptyl, cyclooctyl, bridged cyclic hydrocarbon group, spirohydrocarbon group and the like, preferably, cyclopropyl, cyclobutyl, cyclopentyl, cyclohexyl, bridged cyclic hydrocarbon group and the like.

In the present invention, the "bridged cyclic hydrocarbon group" is, for example, bicyclo[2.1.0]pentyl, bicyclo[2.2.1]heptyl, bicyclo[2.2.2]octyl and bicyclo[3.2.1]octyl, tricyclo[2.2.1.0]heptyl, bicyclo[3.3.1]nonane, 1-adamantyl, 2-adamantyl or the like.

In the present invention, the "spirohydrocarbon group" is, for example, spiro[3.4]octyl or the like.

In the present invention, "cycloalkenyl" includes, for example, a cyclic unsaturated aliphatic hydrocarbon group, and the carbon number is, for example, 3-24 or 3-7. Examples of the aforementioned group include cyclopropenyl, cyclobutenyl, cyclopentenyl, cyclohexenyl, cycloheptenyl and the like, preferably, cyclopropenyl, cyclobutenyl, cyclopentenyl, cyclohexenyl and the like. The aforementioned cycloalkenyl includes, for example, a bridged cyclic hydrocarbon group and a spirohydrocarbon group having an unsaturated bond in the ring.

In the present invention, "arylalkyl" is, for example, benzyl, 2-phenethyl, naphthalenylmethyl or the like, "cycloalkylalkyl" or "cyclylalkyl" is, for example, cyclohexylmethyl, adamantylmethyl or the like, and "hydroxyalkyl" is, for example, hydroxymethyl and 2-hydroxyethyl or the like.

In the present invention, "alkoxy" includes, for example, the aforementioned alkyl-O— group and, for example, methoxy, ethoxy, n-propoxy, isopropoxy, n-butoxy and the like can be mentioned, and "alkoxyalkyl" is, for example, methoxymethyl or the like, and "aminoalkyl" is, for example, 2-aminoethyl or the like.

In the present invention, "cyclyl" is any cyclic atomic group, and is preferably a nonaromatic saturated or unsaturated cyclic substituent. The carbon number thereof is not particularly limited and is, for example, 3-24.

In the present invention, "heterocyclyl" is, for example, 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, tetrahydrofuranyl or the like.

In the present invention, "heterocyclylalkyl" includes, for example, piperidinylmethyl, piperazinylmethyl and the like, "heterocyclylalkenyl" includes, for example, 2-piperidinylethenyl and the like, and "heteroarylalkyl" includes, for example, pyridylmethyl, quinolin-3-ylmethyl and the like.

In the present invention, "silyl" includes, a group represented by the formula $R_3Si-$, wherein R is, independently, selected from the aforementioned alkyl, aryl and cycloalkyl and, for example, a trimethylsilyl group, a tert-butyldimethylsilyl group and the like can be mentioned. The "silyloxy" is, for example, a trimethylsilyloxy group and the like, and "silyloxyalkyl", for example, trimethylsilyloxymethyl or the like.

In the present invention, "alkylene" is, for example, methylene, ethylene, propylene or the like.

In the present invention, "acyl" is not particularly limited and, for example, formyl, acetyl, propionyl, isobutyryl, valeryl, isovaleryl, pivaloyl, hexanoyl, cyclohexanoyl, benzoyl, ethoxycarbonyl, and the like can be mentioned. The same applies to a group containing an acyl group in the structure (acyloxy group, alkanoyloxy group etc.). In the present invention, moreover, the carbon number of the acyl group contains carbonyl carbon and, for example, an alkanoyl group (acyl group) having a carbon number 1 means a formyl group.

In the present invention, "halogen" refers to any halogen element, which is, for example, fluorine, chlorine, bromine or iodine.

In the present invention, "perfluoroalkyl" is not particularly limited and, for example, a perfluoroalkyl group induced from a straight chain or branched alkyl group having 1-30 carbon atoms can be mentioned. The aforementioned "perfluoroalkyl" is more specifically, for example, a perfluoroalkyl group induced from a group such as methyl, ethyl, n-propyl, isopropyl, n-butyl, isobutyl, sec-butyl and tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like. The same applies to a group containing a perfluoroalkyl group in the structure (perfluoroalkylsulfonyl group, perfluoroacyl group etc.).

In the present invention, the aforementioned various groups are optionally substituted. Examples of the aforementioned substituent include hydroxy, carboxy, halogen, alkyl halide (e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), aryl (e.g., phenyl, naphthyl), arylalkyl (e.g., benzyl, phenethyl), heteroaryl (e.g., pyridyl, furyl), heteroarylalkyl (e.g., pyridylmethyl), heterocyclyl (e.g., piperidyl), heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino[alkylamino (e.g., methylamino, ethylamino, dimethylamino), acylamino (e.g., acetylamino, benzoylamino), arylalkylamino (e.g., benzylamino, tritylamino), hydroxyamino], alkylaminoalkyl (e.g., diethylaminomethyl), sulfamoyl, oxo and the like.

In the present invention, when the aforementioned various groups are hetero rings or contain a hetero ring, the "carbon number" also includes the number of hetero atoms constituting the aforementioned hetero ring.

2. Production Method of Thioether

The first production method of thioether in the present invention is, as mentioned above, a method of producing thioether represented by the following chemical formula (103) by a coupling reaction of thiol or thioalkoxide represented by the following chemical formulas (101a) and (101b) with a halide represented by the following chemical formula (102).

Scheme 1

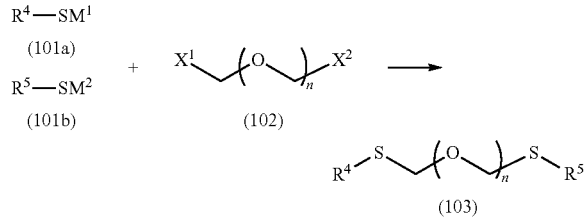

In the aforementioned chemical formulas (101a), (101b) and (103), $R^4$ and $R^5$ are each a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same or different, in the aforementioned chemical formulas (101a) and (101b), $M^1$ and $M^2$ may be the same or different and each is a hydrogen atom or a metal, in the aforementioned chemical formulas (102) and (103), n is a positive integer, and in the aforementioned chemical formula (102), $X^1$ and $X^2$ may be the same or different and each is halogen.

The thioether compound represented by the aforementioned chemical formula (103) can be used as, for example, an intermediate useful for the synthesis of pharmaceutical products. In conventional synthesis methods, the thioether compound (103) could be obtained only in a low yield. However, the present inventors have found a method capable of synthesizing the same in a high yield, and invented the first and the second production methods of the thioether in the present invention. The production method of thioether of the present invention can obtain, for example, the thioether compound (103) in a high yield of not less than 70% relative to the halide (102), as shown in the below-mentioned Example 1.

In the aforementioned chemical formulas (101a), (101b) and (103), $R^4$ and $R^5$ are each a straight chain or branched alkyl group having 1-12 carbon atoms, a straight chain or branched alkenyl group having 2-12 carbon atoms, a straight chain or branched alkynyl group having 2-12 carbon atoms, an aryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, or a straight chain or branched alkoxyalkyl group having 2-30 carbon atoms, and may be preferably the same or different. In addition, in the aforementioned chemical formulas (101a), (101b) and (103), $R^4$ and $R^5$ are particularly preferably methyl groups.

While both $M^1$ and $M^2$ are not particularly limited, for example, hydrogen atom, alkali metal, alkaline earth metal, transition metal and the like can be mentioned, and preferred are hydrogen atom, sodium, potassium, calcium, magnesium, aluminum, zinc, iron, copper, yttrium and bismuth. When $M^1$ and $M^2$ are metals, the valence thereof can be any. In addition, while the atomic number of $M^1$ and $M^2$ is indicated as 1:1 to the molecular number of thiol in the aforementioned chemical formulas (101a) and (101b), it is not limited thereto. For example, when $M^1$ or $M^2$ is an x-valent (x is a positive integer) metal ion, the atomic number of $M^1$ or $M^2$ may be 1/x relative to the molecular number of thiol in the aforementioned chemical formula (101a) or (101b). While the thioalkoxides represented by (101a) and (101b) may be different from each other, they are preferably the same, since it is convenient and preferable for the synthesis of (103).

In the aforementioned chemical formula (102), n is not particularly limited; it is, for example, 1-30, preferably 1-20.

The conditions of the coupling reaction of the thioalkoxides represented by the aforementioned chemical formulas (101a) and (101b), and the halide represented by the aforementioned chemical formula (102) are not particularly limited. While the reaction solvent for the aforementioned coupling reaction is not particularly limited, for example, ketones such as acetone, methyl ethyl ketone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 30 min-4 hr, preferably 30 min-2 hr, more preferably 30 min-1 hr. While the reaction temperature of the aforementioned coupling reaction is not particularly limited, it is, for example, 15-40° C., preferably, 15-37° C., more preferably 20-37° C. Also, the concentration of the thioalkoxides represented by the aforementioned chemical formulas (101a) and (101b), and the halide represented by the aforementioned chemical formula (102) is not particularly limited, and can be appropriately determined. The substance amount ratio of the thioalkoxides represented by the aforementioned chemical formulas (101a) and (101b), and the halide represented by the aforementioned chemical formula (102) is not particularly limited and may be, for example, a stoichiometric mixture ratio or any other ratio. The number of moles of the thioalkoxides represented by the aforementioned chemical formulas (101a) and (101b) is, for example, 1- to 10-fold, preferably 2- to 7-fold, more preferably 3- to 5-fold, of the number of moles of the halide represented by the aforementioned chemical formula (102). The reaction conditions of the aforementioned coupling reaction may be appropriately determined by, for example, referring to the conditions of a known coupling reaction of thioalkoxide and halide and the like, or by reference to the below-mentioned Example 1. Examples of the reference document for known reactions include the reference documents described in the below-mentioned Example 1 and the like.

Examples of the aforementioned coupling reaction include the reactions of the following Scheme 1-2. The reaction of the upper panel of the following Scheme 1-2 is the same as the reaction of the below-mentioned Example 1.

Scheme 1-2

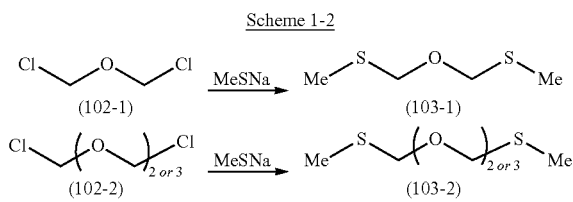

The production method of the halide represented by the aforementioned chemical formula (102) is not particularly limited, either. For example, when a commercially available product of the aforementioned halide, and the like can be obtained, it may be used directly. For example, the compound (102-2) in the aforementioned Scheme 1-2 is commercially available from Aurora Fine Chemicals LLC (US). The aforementioned compound (102-2) can also be synthesized according to, for example, the method of Head, Frank S. H., Journal of the Chemical Society, February, 1012-15, 1965. In addition, the halide represented by the aforementioned chemical formula (102) may also be produced by, for example, hydrolyzing para-formaldehyde with hydrohalic acid and the like. While the reaction solvent for the aforementioned hydrolysis is not particularly limited, for example, water is preferable. For example, halogenated sulfonic acid and the like may be further added to a thick aqueous solution of the aforementioned hydrohalic acid, and the aforementioned hydrolysis may be performed in the system. While the reaction time of the aforementioned hydrolysis is not particularly limited, it is, for example, 1-24 hr, preferably 1-12 hr, more preferably 2-6 hr. While the reaction temperature of the aforementioned hydrolysis is not particularly limited, it is, for example, −20 to 35° C., preferably −10 to 30° C., more preferably −5 to 25° C. The concentration, substance amount ratio and the like of respective reaction substances are not particularly limited likewise, and can be appropriately determined. The reaction conditions of the aforementioned hydrolysis may be appropriately determined by, for example, referring to the conditions of known hydrolysis of para-formaldehyde and the like, or by reference to the below-mentioned Example 1. For example, the compound (102-1) in the aforementioned Scheme 1-2 is the same compound as the compound (1002) in the below-mentioned Example 1, and can be produced according to Example 1. Examples of the reference documents of known reactions include the reference documents described in the below-mentioned Example 1 and the like.

Then, the second production method of the thioether in the present invention is, as mentioned above, a method of producing thioether represented by the following chemical formula (103) by a coupling reaction of the thioether represented by the following chemical formula (103b) and the alcohol represented by the following chemical formula (104) in the presence of a halogenating agent and a Lewis acid.

Scheme 2

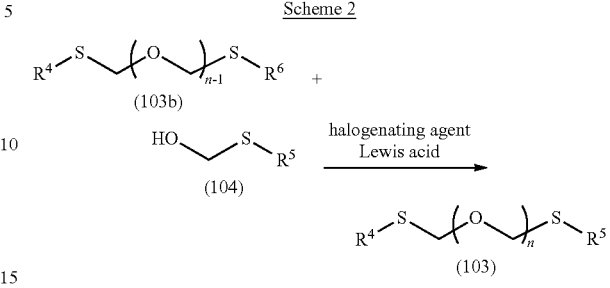

In the aforementioned chemical formulas (103b), (104) and (103), $R^4$, $R^5$ and $R^6$ are each a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same or different, and in the aforementioned chemical formulas (103b) and (103), n is an integer of two or more.

In the aforementioned chemical formulas (103b), (104) and (103), $R^4$, $R^5$ and $R^6$ are each a straight chain or branched alkyl group having 1-12 carbon atoms, a straight chain or branched alkenyl group having 2-12 carbon atoms, a straight chain or branched alkynyl group having 2-12 carbon atoms, an aryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, or a straight chain or branched alkoxyalkyl group having 6-30 carbon atoms, and may be preferably the same or different. In the aforementioned chemical formulas (103b), (104) and (103), $R^4$, $R^5$ and $R^6$ are particularly preferably methyl groups.

In the second production method of the thioether in the present invention, the aforementioned halogenating agent is not particularly limited, but preferably at least one selected from the group consisting of N-chlorosuccinimide, N-bromosuccinimide, N-iodosuccinimide, iodine, bromine and chlorine. Also, the aforementioned Lewis acid is not particularly limited, but preferably at least one selected from the group consisting of perfluoroalkylcarboxylic acid, perfluoroalkylsulfonic acid, alkylsulfonic acid and a salt thereof. The aforementioned Lewis acid is particularly preferably a silver salt of trifluoromethanesulfonic acid. In addition, in the second production method of the thioether in the present invention, the aforementioned coupling reaction is preferably performed in the co-presence of molecular sieve.

In the second production method of the thioether in the present invention, the conditions of the coupling reaction of the thioether represented by the aforementioned chemical formula (103b) and the alcohol represented by the aforementioned chemical formula (104) are not particularly limited. While the reaction solvent for the aforementioned coupling reaction is not particularly limited, for example, ketones such as acetone, methyl ethyl ketone, acetophenone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 1-12 hr, preferably 1-8 hr, more preferably 1-4 hr. While the reaction temperature of the aforementioned coupling reaction is not particularly limited, it is, for example, −75 to 0° C., preferably −60 to −10° C., more preferably −50 to −40° C. The concentrations of the thioether represented by the aforementioned chemical formula (103b) and the alcohol represented by the aforementioned chemical formula (104) are not particularly limited, and can be appropriately determined. The substance amount ratio of the thioether represented by the aforementioned chemical formula (103b) and the alcohol represented by the aforementioned chemical formula (104) is not particularly limited and may be, for example, a stoichiometric mixture ratio or any other ratio. The amount of other reaction substance to be used is not particularly limited. The number of moles of the thioether represented by the aforementioned chemical formula (103b) is, for example, 0.5- to 2-fold, preferably 0.5- to 1-fold, more preferably 0.5-fold, relative to that of the alcohol represented by the aforementioned chemical formula (104). The number of moles of the aforementioned halogenating agent is, for example, 1- to 2-fold, preferably 1- to 1.5-fold, more preferably 1.2-fold, relative to that of the alcohol represented by the aforementioned chemical formula (104). The number of moles of the aforementioned Lewis acid is, for example, 0.005- to 0.05-fold, preferably 0.01- to 0.025-fold, more preferably 0.015-fold, relative to that of the alcohol represented by the aforementioned chemical formula (104). While the amount of the molecular sieve to be used is not particularly limited, it is preferably used in excess against the aforementioned each reaction substance. The reaction conditions of the aforementioned coupling reaction may be appropriately determined by referring to, for example, the conditions of a known coupling reaction of thioether and alcohol, and the like. Examples of the reference document of the known coupling reaction of thioether and alcohol include Eur. Pat. Appl. (1995), EP 639577 A1.

In the second production method of the thioether in the present invention, examples of the aforementioned coupling reaction of thioether and alcohol include the reaction shown in the following Scheme 2-2. In this way, the chain length of thioether can be extended sequentially. In the following Scheme 2-2, "NIS" is N-iodosuccinimide, "TfOAg" is a silver salt of trifluoromethanesulfonic acid, and "MS" is molecular sieve. The compound (105-1) may be synthesized by referring to, for example, Synthetic Communications, 16(13), 1607-10; 1986 and the like, or a commercially available product may be obtained.

3. Ether

The ether of the present invention is, as mentioned above, an ether represented by the following chemical formula (106), an enantiomer thereof, a tautomer or stereoisomer thereof, or a salt thereof.

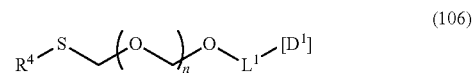

In the aforementioned chemical formula (106), $R^4$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, n is a positive integer, $L^1$ is an ethylene group (—$CH_2CH_2$—), wherein hydrogen atoms besides a hydrogen atom bonded to the α-position relative to [$D^1$] are optionally substituted by a straight chain or branched alkyl group, and

[$D^1$] is an electron-withdrawing group.

In the aforementioned chemical formula (106), $R^4$ is preferably a straight chain or branched alkyl group having 1-12 carbon atoms, a straight chain or branched alkenyl group having 2-12 carbon atoms, a straight chain or branched alkynyl group having 2-12 carbon atoms, an aryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, or a straight chain or branched alkoxyalkyl group having 2-30 carbon atoms. In the aforementioned chemical formula (106), $R^4$ is particularly preferably a methyl group.

In the aforementioned chemical formula (106), the aforementioned straight chain or branched alkyl group for $L^1$ may be, for example, a straight chain or branched alkyl group having 1-12 carbon atoms. $L^1$ is particularly preferably an unsubstituted ethylene group (—$CH_2CH_2$—). In the aforementioned chemical formula (106), [$D^1$] is preferably a cyano group, a nitro group, an alkylsulfonyl group, halogen, a nitro group, an arylsulfonyl group, a trihalomethyl group, or a trialkylamino group. Examples of the aforementioned Scheme 2-2

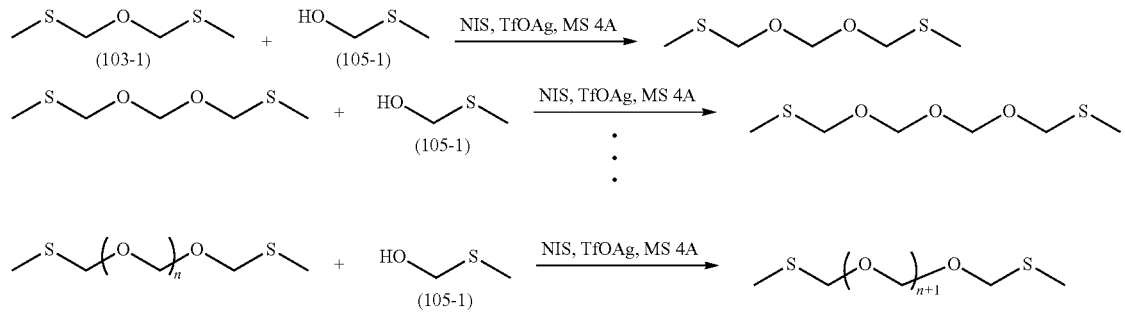

trihalomethyl group include a trichloromethyl group, a trifluoromethyl group and the like. In the aforementioned chemical formula (106), n is not particularly limited and, for example, within the range of 1-30, preferably 1-20.

The ether represented by the aforementioned chemical formula (106) of the present invention is preferable as a synthesis intermediate for the aforementioned glycoside compound of the present invention. However, the ether of the present invention is not limited thereto and may be used for any use.

4. Production Method of Ether

While the production method of the ether represented by the aforementioned chemical formula (106) of the present invention is not particularly limited, the aforementioned production method of the ether of the present invention is preferable. The production method of the ether of the present invention is, as mentioned above, a method of producing the ether represented by the aforementioned chemical formula (106) of the present invention by a coupling reaction of the thioether represented by the following chemical formula (103) and the alcohol represented by the following chemical formula (105) in the presence of a halogenating agent and a Lewis acid.

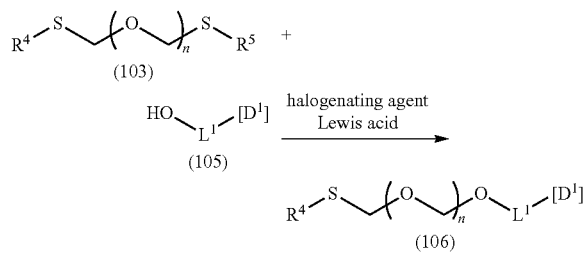

Scheme 3

In the aforementioned chemical formulas (103) and (105), $R^4$ is as defined for the aforementioned chemical formula (106), $R^5$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same as or different from $R^4$, in the aforementioned chemical formula (103), n is as defined for the aforementioned chemical formula (106), and in the aforementioned chemical formula (105), $L^1$ and $[D^1]$ are as defined for the aforementioned chemical formula (106).

In the aforementioned chemical formula (103), $R^5$ is a straight chain or branched alkyl group having 1-12 carbon atoms, a straight chain or branched alkenyl group having 2-12 carbon atoms, a straight chain or branched alkynyl group having 2-12 carbon atoms, an aryl group having 5-24 carbon atoms, a straight chain or branched arylalkyl group having 6-30 carbon atoms, a cycloalkyl group having 3-24 carbon atoms, a cycloalkenyl group having 3-24 carbon atoms, a straight chain or branched cycloalkylalkyl group having 4-30 carbon atoms, a straight chain or branched cyclylalkyl group having 4-30 carbon atoms, or a straight chain or branched alkoxyalkyl group having 2-30 carbon atoms, and may be preferably the same or different. In the aforementioned chemical formula (103), $R^5$ is particularly preferably a methyl group.

In the production method of the ether of the present invention, the aforementioned halogenating agent is not particularly limited, and is preferably at least one selected from the group consisting of N-chlorosuccinimide, N-bromosuccinimide, N-iodosuccinimide, iodine, bromine and chlorine. Also, the aforementioned Lewis acid is not particularly limited, but it is preferably at least one selected from the group consisting of perfluoroalkylcarboxylic acid, perfluoroalkylsulfonic acid, alkylsulfonic acid and a salt thereof. The aforementioned Lewis acid is particularly preferably a silver salt of trifluoromethanesulfonic acid. In addition, in the second production method of the thioether in the present invention, the aforementioned coupling reaction is preferably performed in the co-presence of molecular sieve.

In the production method of the ether of the present invention, the conditions of the coupling reaction of the thioether represented by the aforementioned chemical formula (103) and the alcohol represented by the aforementioned chemical formula (105) are not particularly limited. While the reaction solvent for the aforementioned coupling reaction is not particularly limited, for example, ketones such as acetone, methyl ethyl ketone, acetophenone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 1-12 hr, preferably 1-8 hr, more preferably 1-4 hr. While the reaction temperature of the aforementioned coupling reaction is not particularly limited, it is, for example, −75 to 0° C., preferably −60 to −10° C., more preferably −50 to −40° C. The concentration of the thioether represented by the aforementioned chemical formula (103) and the alcohol represented by the aforementioned chemical formula (105) is not particularly limited, and can be appropriately determined. The substance amount ratio of the thioether represented by the aforementioned chemical formula (103) and the alcohol represented by the aforementioned chemical formula (105) is not particularly limited and may be, for example, a stoichiometric mixture ratio or any other ratio. Also, the amount of other reaction substance to be used is not particularly limited. The number of moles of the thioether represented by the aforementioned chemical formula (103) is, for example, 0.5- to 2-fold, preferably 0.5- to 1-fold, more preferably 0.5-fold, relative to that of the alcohol represented by the aforementioned chemical formula (105). The number of moles of the aforementioned halogenating agent is, for example, 1- to 2-fold, preferably 1- to 1.5-fold, more preferably 1.2-fold, relative to that of the alcohol represented by the aforementioned chemical formula (105). The number of moles of the aforementioned Lewis acid is, for example, 0.005- to 0.05-fold, preferably 0.01- to 0.025-fold, more preferably 0.015-fold, relative to that of the alcohol represented by the aforementioned chemical formula (105). While the amount of the molecular sieve to be used is not particularly limited, it is preferably used in excess against the aforementioned each reaction substance. The reaction conditions of the aforementioned coupling reaction may be appropriately determined by referring to, for example, the conditions of a known coupling reaction of thioether and alcohol, and the like, or by reference to the below-mentioned Example 1. Examples of the reference document for the known coupling reaction of thioether and alcohol include Eur. Pat. Appl. (1995), EP 639577 A1.

In the production method of the ether of the present invention, the production method of the thioether represented by the aforementioned chemical formula (103) is not particularly limited, and it is preferably the aforementioned first or second production method of the thioether in the present invention. That is, the production method of the ether represented by the aforementioned chemical formula (106) of the present invention preferably further includes a step of producing the thioether represented by the aforementioned chemical formula (103) according to the aforementioned first or second production method of the thioether in the present invention.

5. Production Method of Glycoside Compound

The production method of the glycoside compound of the present invention is not particularly limited and can be appropriately performed by referring to, for example, a known production method of glycoside (ACE amidite etc.). For example, the production method described in Current Protocols in Nucleic Acid Chemistry, unit 2.16.1-2.16.31 (2009). may be referred to.

The glycoside of the present invention is preferably produced by, for example, the aforementioned production method of the present invention (production method of glycoside compound). The aforementioned production method of the present invention (production method of the glycoside compound) includes, as mentioned above, a coupling step including a coupling reaction of a glycoside compound represented by the following chemical formula (107) and an ether represented by the following chemical formula (106), in the presence of a halogenating agent and a Lewis acid to give a glycoside compound represented by the following chemical formula (1a). The glycoside compound represented by the following chemical formula (1a) is a glycoside compound wherein $R^1$ and $R^2$ in the aforementioned chemical formula (1) in conjunction form an atomic group represented by the aforementioned chemical formula $(R^1R^2A)$ or $(R^1R^2B)$.

Scheme 4

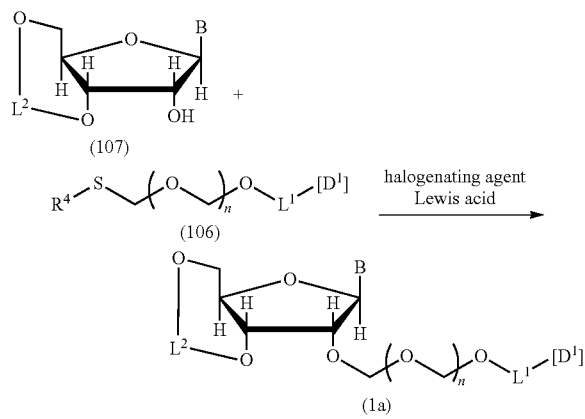

In the aforementioned chemical formulas (107) and (1a),
$L^2$ is an atomic group represented by the aforementioned chemical formula $(R^1R^2A)$ or $(R^1R^2B)$,
B is as defined for the aforementioned chemical formula (1),
in the aforementioned chemical formula (106),
$R^4$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, and
in the aforementioned chemical formula (106) and (1a),
$L^1$, n and $[D^1]$ are as defined for the aforementioned chemical formula (1).

The method of obtaining the glycoside represented by the aforementioned chemical formula (107) is not particularly limited and, for example, it may be obtained as a commercially available product or may be produced by a known method. In the aforementioned coupling reaction (the aforementioned Scheme 4), the aforementioned halogenating agent is not particularly limited, but preferably at least one selected from the group consisting of N-chlorosuccinimide, N-bromosuccinimide, N-iodosuccinimide, iodine, bromine and chlorine. Also, the aforementioned Lewis acid is not particularly limited, but preferably at least one selected from the group consisting of perfluoroalkylcarboxylic acid, perfluoroalkylsulfonic acid, alkylsulfonic acid and a salt thereof. The aforementioned Lewis acid is particularly preferably trifluoromethanesulfonic acid or a salt thereof.

In the production method of the glycoside compound of the present invention, the conditions of the coupling reaction of the thioether represented by the aforementioned chemical formula (107) and the ether represented by the aforementioned chemical formula (106) are not particularly limited. While the reaction solvent for the aforementioned coupling reaction is not particularly limited, for example, ketones such as acetone, methyl ethyl ketone, acetophenone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 1-12 hr, preferably 1-8 hr, more preferably 1-4 hr. While the reaction temperature of the aforementioned coupling reaction is not particularly limited, it is, for example, −75 to 0° C., preferably −60 to −10° C., more preferably −50 to −40° C. The concentration of the glycoside compound represented by the aforementioned chemical formula (107) and the ether represented by the aforementioned chemical formula (106) is not particularly limited, and can be appropriately determined. The substance amount ratio of the glycoside compound represented by the aforementioned chemical formula (107) and the ether represented by the aforementioned chemical formula (106) is not particularly limited and may be, for example, a stoichiometric mixture ratio or any other ratio. Also, the amount of other reaction substance to be used is not particularly limited. The number of moles of the glycoside compound represented by the aforementioned chemical formula (107) is, for example, 1- to 5-fold, preferably 1- to 3-fold, more preferably 1- to 1.5-fold, relative to that of the ether represented by the aforementioned chemical formula (106). The number of moles of the aforementioned halogenating agent is, for example, 1- to 3-fold, preferably 1- to 2-fold, more preferably 1- to 1.5-fold, relative to that of the ether represented by the aforementioned chemical formula (106). The number of moles of the aforementioned Lewis acid is, for example, 0.005- to 0.05-fold, preferably 0.01- to 0.025-fold, more preferably 0.015-fold, relative to that of the ether represented by the aforementioned chemical formula (106). The reaction conditions of the aforementioned coupling reaction may be appropriately determined by referring to, for example, as mentioned above, the conditions of a known amidite synthesis of the glycoside compound, and the like, or by reference to any of the below-mentioned Examples 2 to 5.

The production method of the glycoside compound of the present invention preferably further includes a deprotection step for removing the aforementioned atomic group $L^2$ from the glycoside compound represented by the aforementioned chemical formula (1a) to produce glycoside compound represented by the following chemical formula (1b). In this case, the glycoside compound represented by the following chemical formula (1b) is a glycoside compound of the aforementioned chemical formula (1) wherein $R^1$ and $R^2$ are hydrogen atoms.

Scheme 5

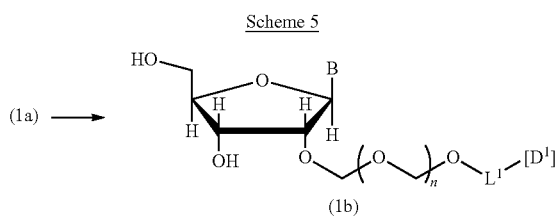

In the aforementioned chemical formula (1b),
B, $L^1$, n and $[D^1]$ are as defined for the aforementioned chemical formula (1).

In the aforementioned deprotection step, while the conditions of the deprotection are not particularly limited, for example, a known deprotecting agent can be used. While the aforementioned deprotecting agent is not particularly limited, for example, hydrogen fluoride pyridine, hydrogen fluoride triethylamine, ammonium fluoride, hydrofluoric acid, tetrabutylammoniumfluoride and the like can be mentioned. While the reaction solvent for the aforementioned deprotection is not particularly limited, for example, ketones such as acetone and the like, ethers such as diethyl ether, THF (tetrahydrofuran) and the like, alcohols such as methanol, ethanol and the like, nitriles such as acetonitrile etc., and the like can be mentioned. While the reaction time of the aforementioned deprotection is not particularly limited, it is, for example, 30 min-24 hr, preferably 2-12 hr, more preferably 2-4 hr. While the reaction temperature of the aforementioned deprotection is not particularly limited, it is, for example, 0 to 100° C., preferably 20 to 60° C., more preferably 20 to 50° C. The concentration of the glycoside compound represented by the aforementioned chemical formula (1a) and the aforementioned deprotecting agent is not particularly limited, and can be appropriately determined. The substance amount ratio of the glycoside compound represented by the aforementioned chemical formula (1a) and the aforementioned deprotecting agent is not particularly limited and may be, for example, a stoichiometric mixture ratio or any other ratio. Also, the amount of other reaction substance to be used is not particularly limited. The number of moles of the aforementioned deprotecting agent is, for example, 0.1- to 20-fold, preferably 0.2- to 10-fold, more preferably 1- to 5-fold, relative to that of the glycoside compound represented by the aforementioned chemical formula (1a). The reaction conditions of the aforementioned deprotection may be appropriately determined by referring to, for example, the conditions of a similar deprotection in a known glycoside compound, and the like, or by reference to any of the below-mentioned Examples 2 to 5.

The production method of the glycoside compound of the present invention preferably further includes an introduction step of a protecting group for introducing protecting groups $R^1$ and $R^2$ into the aforementioned chemical formula (1b) to produce glycoside compound represented by the following chemical formula (1c). In this case, the glycoside compound represented by the following chemical formula (1c) is a glycoside compound of the aforementioned chemical formula (1) wherein $R^1$ and $R^2$ are except for hydrogen atoms, the aforementioned chemical formulas ($R^1R^2A$) and ($R^1R^2B$).

Scheme 6

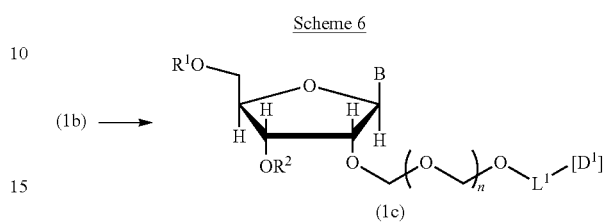

In the aforementioned chemical formula (1c),
$R^1$ and $R^2$ are $R^1$ and $R^2$ in the aforementioned chemical formula (1) but excluding a hydrogen atom and the aforementioned chemical formulas ($R^1R^2A$) and ($R^1R^2B$), and
B, $L^1$, n and $[D^1]$ are as defined for the aforementioned chemical formula (1).

The reaction conditions of the aforementioned protecting group introduction step are not particularly limited and may be appropriately determined, for example, by referring to a similar reaction in a known glycoside compound and the like. In the aforementioned protecting group introduction step, for example, the aforementioned $R^1$ and $R^2$ may be simultaneously (in one step) introduced, or $R^2$ may be added after introduction of $R^1$, or $R^1$ may be introduced after introduction of $R^2$. For example, it is preferable to introduce $R^2$ after introduction of $R^1$. While the protecting groups $R^1$ and $R^2$ are not particularly limited, for example, they are as mentioned above.

In an introduction reaction of the protecting group $R^1$, a protecting group-introducing agent may be appropriately selected according to $R^1$. While the reaction solvent is not particularly limited, for example, polar solvents such as pyridine and the like, nitriles such as acetonitrile and the like, ethers such as tetrahydrofuran etc., and the like can be mentioned. While the reaction time is not particularly limited, it is, for example, 30 min-24 hr, preferably 2-12 hr, more preferably 2-4 hr. While the reaction temperature is not particularly limited, it is, for example, 0 to 100° C., preferably 10 to 60° C., more preferably 20 to 30° C. The concentration of the glycoside compound to be used and the protecting group-introducing agent is not particularly limited, and can be appropriately determined. The substance amount ratio of the aforementioned glycoside compound and the aforementioned protecting group-introducing agent is not particularly limited and may be, for example, a stoichiometric mixture ratio or any other ratio. Also, the amount of other reaction substance to be used is not particularly limited. The number of moles of the aforementioned protecting group-introducing agent is, for example, 1- to 100-fold, preferably 1- to 20-fold, more preferably 1- to 5-fold, relative to that of the aforementioned glycoside compound. The reaction conditions of the introduction reaction of a protecting group $R^1$ may be appropriately determined by referring to, for example, the conditions of a similar reaction in a known glycoside compound, and the like, or by reference to any of the below-mentioned Examples 2 to 5.

In the introduction reaction of the protecting group $R^2$, the protecting group-introducing agent may be appropriately selected according to $R^2$. While the reaction solvent is not particularly limited, for example, nitriles such as acetonitrile and the like, ethers such as tetrahydrofuran, halogenated solvents such as dichloromethane etc., and the like can be mentioned. While the reaction time is not particularly limited, it is, for example, 30 min-24 hr, preferably 1-12 hr, more preferably 4-6 hr. While the reaction temperature is not particularly limited, it is, for example, −80 to 30° C., preferably −70 to 0° C., more preferably −50 to −40° C. The concentration of the glycoside compound to be used and the protecting group-introducing agent is not particularly limited, and can be appropriately determined. The substance amount ratio of the aforementioned glycoside compound and the aforementioned protecting group-introducing agent is not particularly limited and may be, for example, a stoichiometric mixture ratio or any other ratio. Also, the amount of other reaction substance to be used is not particularly limited. The number of moles of the aforementioned protecting group-introducing agent is, for example, 1- to 20-fold, preferably 1- to 5-fold, more preferably 1- to 1.5-fold, relative to that of the aforementioned glycoside compound. The reaction conditions of the introduction reaction of a protecting group $R^2$ may be appropriately determined by referring to, for example, the conditions of a similar reaction in a known glycoside compound, and the like, or by reference to the below-mentioned Example 2 or 3.

Also, in each of the aforementioned reaction steps, the purification method of the reaction product is not particularly limited and the method can be appropriately performed by reference to a known method and the like.

In the production method of the glycoside compound of the present invention, the ether represented by the aforementioned chemical formula (106) is more preferably produced by the aforementioned production method of ether of the present invention. In addition, thioether (103), which is an intermediate therefor, is more preferably produced by the aforementioned first or second production method of the thioether in the present invention. In this way, the glycoside compound of the present invention can be obtained in a still higher yield.

6. Production Method of Nucleic Acid

The production method of a nucleic acid of the present invention is, as mentioned above, a production method of a nucleic acid having the structure represented by the following chemical formula (I), and characteristically includes a condensation step for a condensation reaction of the glycoside compound of the present invention represented by the aforementioned chemical formula (1), wherein the glycoside compound is a glycoside compound represented by the aforementioned chemical formula (2).

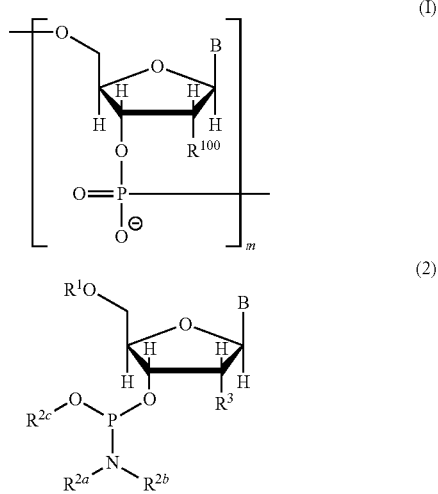

In the aforementioned chemical formula (I), B is as defined for the aforementioned chemical formula (1), (2) or (3), $R^{100}$ is a hydrogen atom or a hydroxyl group, respective B may be the same or different, and respective $R^{100}$ may be the same or different, and m is a positive integer.

The reaction conditions of the production method of a nucleic acid of the present invention are not particularly limited and, for example, the method can be performed in the same manner as in general phosphoramidite method and the like. For example, the production method of a nucleic acid of the present invention may include production (synthesis) by a general automatic synthesizer of nucleic acid and the like. That is, the glycoside compound represented by the aforementioned chemical formula (2) of the present invention can be used as an amidite for an automatic nucleic acid synthesizer. Using the glycoside compound represented by the aforementioned chemical formula (2) of the present invention, the production method of a nucleic acid of the present invention can produce a nucleic acid with high purity and in a high yield. Specifically, for example, RNA can be synthesized with purity comparable to that in DNA synthesis. While the reason therefor is not clear, for example, improved efficiency of the condensation reaction (coupling reaction) due to less steric hindrance during condensation reaction (coupling reaction) as compared to TBDMS amidite, TOM amidite, ACE amidite and the like, and the like are considered. Moreover, the glycoside compound represented by the aforementioned chemical formula (2) of the present invention permits easy deprotection associated with the condensation reaction (coupling reaction).

In the production method of a nucleic acid of the present invention, for example, the nucleic acid having the structure represented by the aforementioned chemical formula (I) may be a nucleic acid represented by the following chemical formula (II):

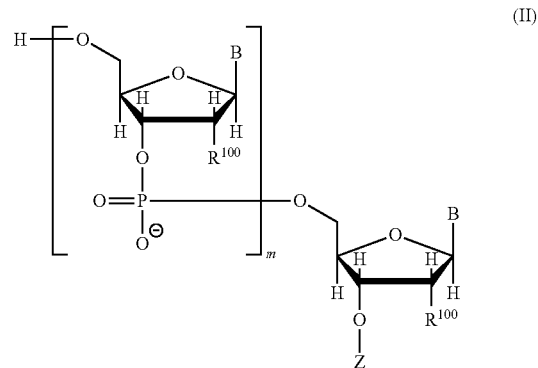

in the aforementioned chemical formula (II),

B, $R^{100}$ and m are as defined for the aforementioned chemical formula (I), respective B may be the same or different, respective $R^{100}$ may be the same or different, and Z is a hydrogen atom or a phosphate group, and the production method may contain the following steps A1-A6.

[Step A1]

A step of producing the glycoside compound represented by the following chemical formula (202) by reacting an acid with the glycoside compound represented by the following chemical formula (201), and deprotecting the hydroxyl group of the 5' position.

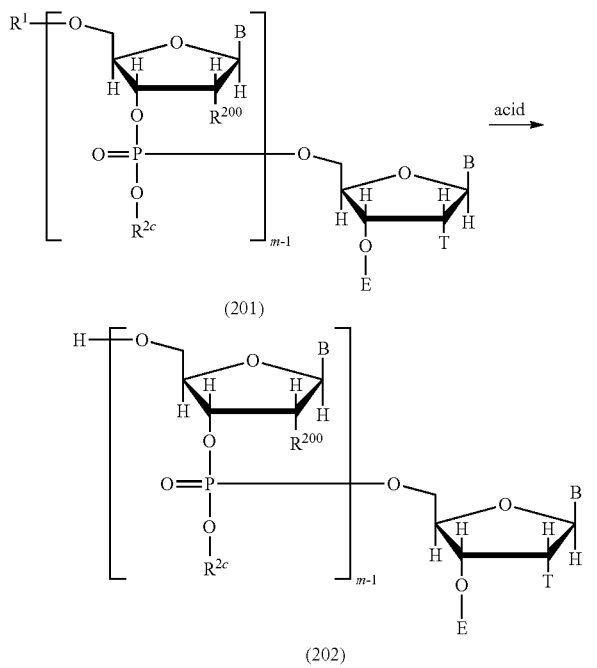

(201)

(202)

In the aforementioned chemical formulas (201) and (202), m and B are as defined for the aforementioned chemical formula (II), $R^1$ and $R^{2c}$ are as defined for the aforementioned chemical formula (2), respective $R^{200}$ may be the same or different and each is a hydrogen atom, an acyloxy group or a substituent represented by the following chemical formula (203), T is a hydrogen atom, an acyloxy group, or a substituent represented by the following chemical formula (203) or (204), E is an acyl group or a substituent represented by the following chemical formula (204), at least one of E and T is a substituent represented by the following chemical formula (204),

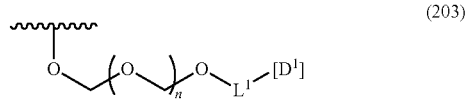

(203)

in the aforementioned chemical formula (203), $[D^1]$, $L^1$ and n are as defined for the aforementioned chemical formula (2),

(204)

in the aforementioned chemical formula (204), $L^3$ is a linker, [S] is a solid phase carrier, Q is a single bond or a substituent represented by the following chemical formula (205),

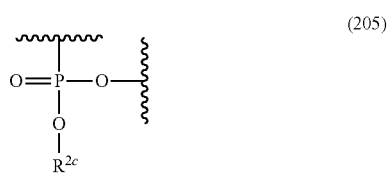

(205)

in the aforementioned chemical formula (205), $R^{2c}$ is as defined for the aforementioned chemical formula (2).

In the aforementioned chemical formulas (201) and (202), examples of the aforementioned acyl group for E include an acetyl group, a propionyl group, a butyryl group, an isobutyryl group, a benzoyl group, a 4-methoxybenzoyl group, a phenylacetyl group, a phenoxyacetyl group, a 4-tert-butylphenoxyacetyl group, a 4-isopropylphenoxyacetyl group and the like. The acyl group in the aforementioned acyloxy group for T and $R^{200}$ is also the same.

In the aforementioned chemical formula (204), examples of the aforementioned $L^3$ (linker) include a group induced from any of a 3-aminopropyl group, a long chain alkylamino (LCAA) group and 2-(2-hydroxyethylsulfonyl)ethanol, a succinyl group and the like. Examples of the aforementioned [S] (solid phase carrier) include controlled pore glass (CPG), oxalylated controlled pore glass (see Alul et al., Nucleic Acids Research, Vol. 19, 1527 (1991), etc.), TentaGel support-aminopolyethylene glycol derivatization support (see Wright et al., Tetrahedron Letters, Vol. 34, 3373 (1993), etc.), a copolymer of porous polystyrene and divinylbenzene and the like.

In the aforementioned chemical formulas (201) and (202), preferably, T is a substituent represented by the aforementioned chemical formula (203), and E is a compound represented by the following chemical formula (204-1) or (204-2).

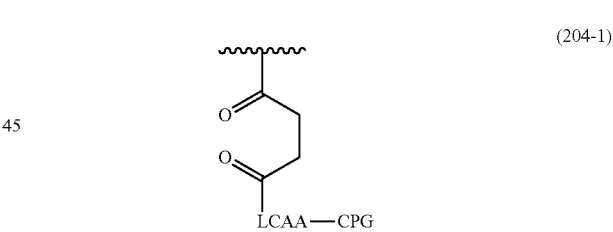

(204-1)

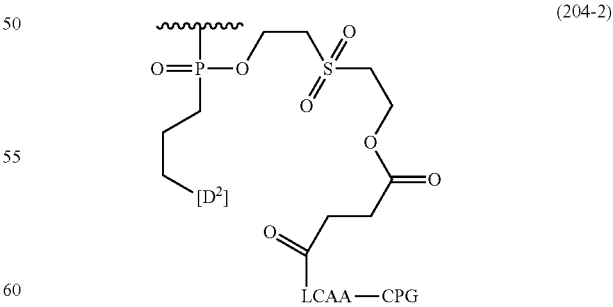

(204-2)

In the aforementioned chemical formulas (204-1) and (204-2), LCAA and CPG are as defined for the aforementioned chemical formula (204). In the aforementioned chemical formula (204-2), $[D^2]$ is as defined for the aforementioned chemical formula (2).

While the aforementioned acid to be used for step A1 is not particularly limited, for example, halogenated carboxylic acid and the like can be mentioned. Examples of the aforementioned halogenated carboxylic acid include trifluoroacetic acid, dichloroacetic acid, trichloroacetic acid and the like. The aforementioned acid may be used, for example, after dissolving in a suitable solvent. While the concentration of the solution is not particularly limited, it is, for example, 1-5 wt %. While the aforementioned solvent is not particularly limited, for example, halogenated solvents such as dichloromethane and the like, nitriles such as acetonitrile and the like, water and the like can be mentioned. These may be used alone or plural kinds thereof may be used in combination. While the reaction temperature in step A1 is not particularly limited, 20° C.-50° C. is preferable. While the reaction time is not particularly limited and varies depending on the kind of the acid to be used, reaction temperature and the like, it is, for example, 1 min-1 hr. Also, while the amount of the aforementioned acid to be used (number of moles) is not particularly limited, it is, for example, 1- to 100-fold, preferably 1- to 10-fold, relative to the number of moles of the sugar (or base) in the aforementioned glycoside compound (201).

[Step A2]

A step of producing the glycoside compound represented by the following chemical formula (206) by condensing the glycoside compound (202) produced in the aforementioned step A1 with a nucleic acid monomer compound in the presence of an activator.

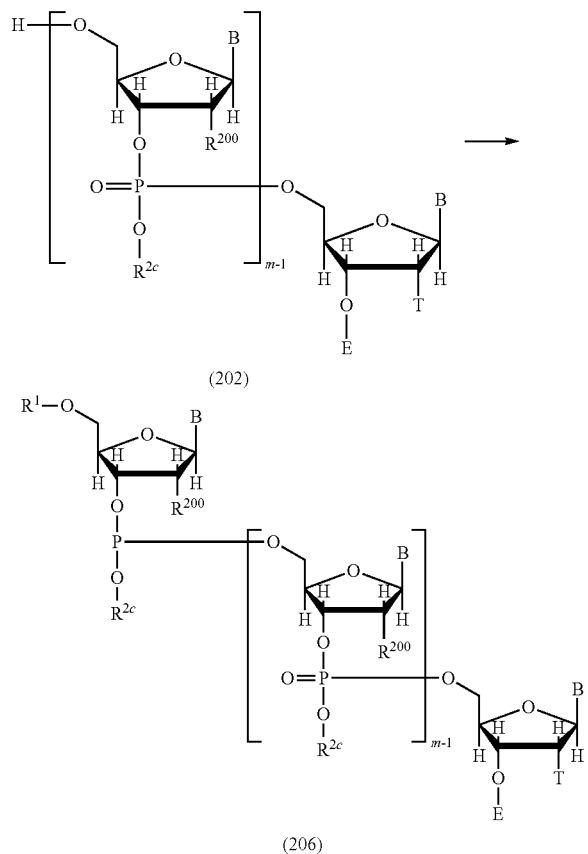

In the aforementioned chemical formula (206),

B, E, m, $R^1$, $R^{200}$, T and $R^{2c}$ are as defined for the aforementioned chemical formula (201), respective B, respective $R^{200}$ and respective $R^{2c}$ may be the same or different.

Examples of the aforementioned "nucleic acid monomer compound" in step A2 include the glycoside compound represented by the aforementioned chemical formula (2) of the present invention. While it is possible to use other glycoside compounds as the aforementioned "nucleic acid monomer compound", the glycoside compound represented by the aforementioned chemical formula (2) is preferably used from the aspects of reaction efficiency, yield of the object resultant product, purity of the object resultant product and the like. Moreover, the glycoside compound represented by the aforementioned chemical formula (2) may be used along with other glycoside compound. Examples of the aforementioned "other glycoside compound" include a glycoside compound of the aforementioned chemical formula (2) wherein $R^3$ is changed to H (hydrogen atom) or OH (hydroxyl group). In the production method of a nucleic acid of the present invention, 1 molecule or more at minimum of the glycoside compound represented by the aforementioned chemical formula (2) of the present invention is used to produce a nucleic acid. As mentioned below, moreover, the condensation reaction may be repeated plural times in Step A2 by repeating steps A1-A4 appropriate times. In this way, the chain length of the object nucleic acid (glycoside compound (I) or (II)) can be a desired (given) chain length. In the production method of a nucleic acid of the present invention, the glycoside compound represented by the aforementioned chemical formula (2) of the present invention is preferably subjected to plural molecule polymerization (condensation polymerization). In this way, for example, RNA (i.e., nucleic acid of the aforementioned chemical formulas (I) or (II), wherein each $R^{100}$ is a hydroxyl group) can be synthesized (produced). Alternatively, DNA (nucleic acid of the aforementioned chemical formulas (I) or (II), wherein each $R^{100}$ is a hydrogen atom) can be synthesized by, for example, reverse transcription of RNA synthesized by plural molecule polymerization (condensation polymerization) of the glycoside compound represented by the aforementioned chemical formula (2) of the present invention. The nucleic acid of the aforementioned chemical formulas (I) or (II), which includes $R^{100}$ as a hydrogen and $R^{100}$ as a hydroxyl group may be synthesized by, for example, a condensation reaction of the glycoside compound represented by the aforementioned chemical formula (2) and the glycoside compound of the aforementioned chemical formula (2) wherein $R^3$ is changed to H (hydrogen atom).

In step A2, the aforementioned activator is not particularly limited and, for example, may be an activator similar to that used for known nucleic acid synthesis. Examples of the aforementioned activator include 1H-tetrazole, 5-ethylthiotetrazole, 4,5-dichloroimidazole, 4,5-dicyanoimidazole, benzotriazole triflate, imidazole triflate, pyridinium triflate, N,N-diisopropylethylamine, 2,4,6-collidine/N-methylimidazole and the like.

In step A2, while the reaction solvent is not particularly limited, for example, nitriles such as acetonitrile and the like, ethers such as tetrahydrofuran, dioxane etc., and the like can be mentioned. These solvents may be used alone or plural kinds thereof may be used in combination. While the reaction temperature is not particularly limited, 20° C.-50° C. is preferable. Also, while the reaction time is not particularly limited and varies depending on the kind of the activator to be used, reaction temperature and the like, it is, for example, 1 min-1 hr. While the amount of the aforementioned nucleic acid monomer compound to be used (number of moles) is not particularly limited, it is, for example, 1- to 100-fold, preferably 1- to 10-fold, relative to the number of moles of the sugar (or base) in the aforementioned glycoside compound (202). The amount of the aforementioned activator to be used is also the same.

[Step A3]

A step of capping the hydroxyl group at the 5'-position of the aforementioned glycoside compound (202), which was unreacted in the aforementioned step A2.

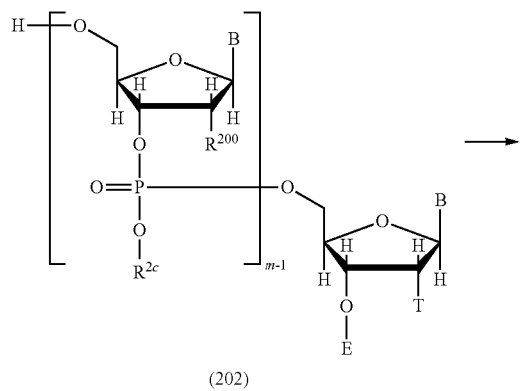
(202)

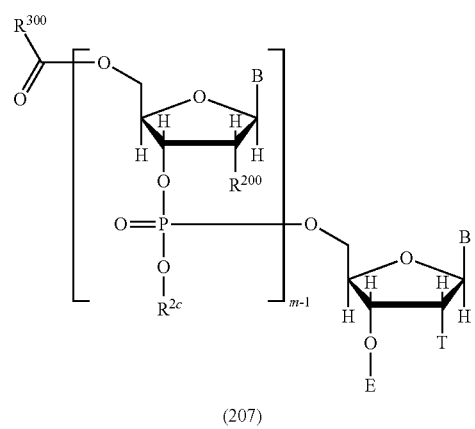
(207)

In the aforementioned chemical formula (207),
$R^{300}$ is a methyl group or a phenoxymethyl group, and B, E, m, $R^{200}$, T and $R^{2c}$ are as defined for the aforementioned chemical formula (5).

In step A3, the hydroxyl group at the 5'-position, which was unreacted on completion of the aforementioned step A2, is protected by reacting with a capping agent. While the aforementioned capping agent is not particularly limited, for example, acetic anhydride, phenoxyacetic acid anhydride and the like can be mentioned. For example, the aforementioned capping agent may be used in the form of a solution. While the solvent of the aforementioned solution is not particularly limited, for example, pyridine, dichloromethane, acetonitrile, tetrahydrofuran, a mixed solvent thereof and the like can be mentioned. While the concentration of the aforementioned solution is not particularly limited, it is, for example, 0.05-1M. In step A3, for example, an appropriate reaction accelerator such as 4-dimethylaminopyridine, N-methylimidazole and the like may also be used in combination. While the reaction temperature is not particularly limited, 20° C.-50° C. is preferable. Also, while the reaction time is not particularly limited and varies depending on the kind of the capping agent to be used, reaction temperature and the like, it is, for example, 1-30 min. While the amount of the aforementioned capping agent to be used (number of moles) is not particularly limited, it is, for example, 1- to 100-fold, preferably 1- to 10-fold, relative to the number of moles of the sugar (or base) in the aforementioned glycoside compound (202). The amount of the aforementioned activator to be used is also the same. The amount of the aforementioned reaction accelerator to be used is also the same.

[Step A4]

A step of converting a phosphorous acid group in the aforementioned chemical formula (206) into a phosphate group by reacting the glycoside compound (206) produced in the aforementioned step A2 with an oxidant.

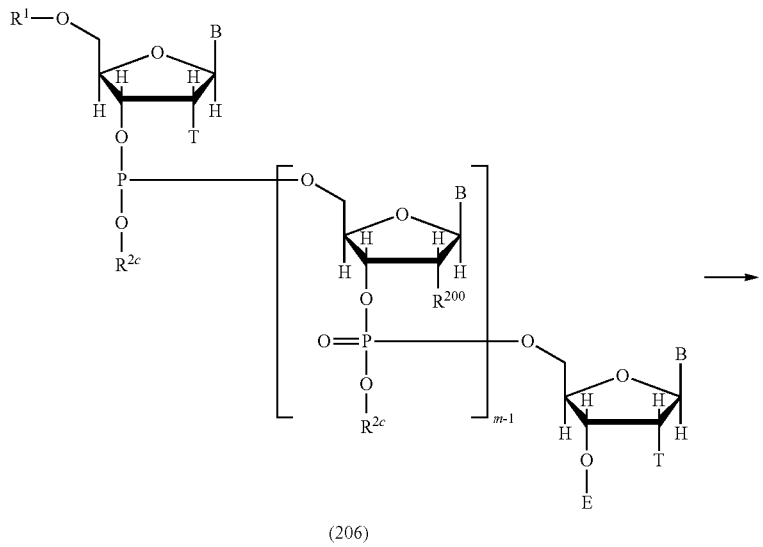
(206)

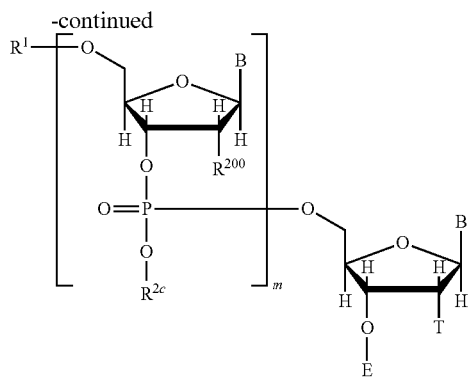

(208)

In the aforementioned chemical formula (208),
B, E, m, $R^1$, $R^{200}$, T and $R^{2c}$ are as defined for the aforementioned chemical formula (206).

While the aforementioned oxidant in step A4 is not particularly limited, for example, iodine, peroxide (e.g., tert-butyl hydroperoxide) and the like can be mentioned. The aforementioned oxidant may be used in the form of a solution. While the solvent for the aforementioned solution is not particularly limited, for example, pyridine, tetrahydrofuran, water, acetic acid, methylene chloride, a mixed solvent thereof and the like can be mentioned. As the aforementioned solution, a solution obtained by dissolving iodine in a mixed solvent of water, pyridine and tetrahydrofuran, a solution obtained by dissolving iodine in a mixed solvent of pyridine and acetic acid, a solution obtained by dissolving d peroxide in methylene chloride and the like can be used. While the concentration of the aforementioned solvent is not particularly limited, it is, for example, 0.05-2M. While the reaction temperature is not particularly limited, 20° C.-50° C. is preferable. Also, while the reaction time is not particularly limited and varies depending on the kind of the oxidant to be used, reaction temperature and the like, it is, for example, 1-30 min. While the amount of the aforementioned oxidant to be used (number of moles) is not particularly limited, it is, for example, 1- to 100-fold, preferably 1- to 10-fold, relative to the number of moles of the sugar (or base) in the aforementioned glycoside compound (206).

After step A4 and before performing the next step A5, the operation may return to step A1. By repeating steps A1-A4 an appropriate number of times in this way, the chain length of the object nucleic acid (glycoside compound (208)) can become a desired (given) chain length.

[Step A5]

A step of cleaving the glycoside compound (208) produced in the aforementioned step A4 from the aforementioned solid phase carrier, and deprotecting each nucleic acid base region and the hydroxyl group at each 2'-position.

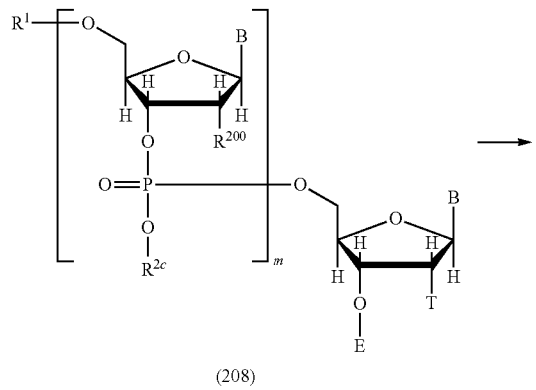

(208)

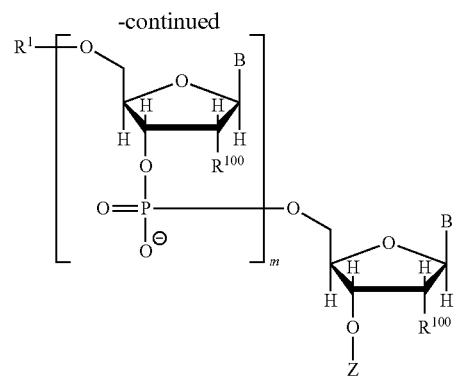

(209)

In the aforementioned chemical formula (209),
B, m, $R^1$ and $R^{200}$ are as defined for the aforementioned chemical formula (208), and
$R^{100}$ and Z are as defined for the aforementioned chemical formula (II).

In step A5, a step for cleaving the aforementioned glycoside compound (208), namely, a nucleic acid with a given chain length, from a solid phase carrier (cleaving step) can be performed by adding a cleaving agent to a solid carrier carrying the aforementioned nucleic acid (208). While the aforementioned cleaving agent is not particularly limited, for example, conc. aqueous ammonia, methylamine and the like can be mentioned. One kind or two or more kinds may be used in combination. The aforementioned cleaving agent may be used by, for example, dissolving in a solvent. While the aforementioned solvent is not particularly limited, for example, water, methanol, ethanol, isopropyl alcohol, acetonitrile, tetrahydrofuran, a mixed solvent thereof and the like can be mentioned, with particular preference given to ethanol. While the concentration of the aforementioned solution is not particularly limited, for example, the concentration of ammonium hydroxide in the aforementioned solution is set to 20-30 wt %. The concentration of the aforementioned ammonium hydroxide is preferably 25-30 wt %, more preferably 28-30 wt %. While the amount of the aforementioned cleaving agent to be used (number of moles) is not particularly limited, it is, for example, 1- to 100-fold, preferably 1- to 10-fold, relative to the number of moles of the sugar (or base) in the aforementioned glycoside compound (208). The amount of the aforementioned activator to be used is also the same. While the reaction temperature of the aforementioned cleaving step is not particularly limited, it is, for example, 15° C. to 75° C., preferably 15° C. to 50° C., more preferably 15° C. to 30° C., more preferably 18° C. to 25° C., more preferably 20° C. to 25° C. While the reaction time is not particularly limited and varies depending on the kind of the oxidant, reaction temperature and the like, it is, for example, 1-24 hr.

In the aforementioned deprotection step of the hydroxyl group at the 2'-position in step A5, while the deprotecting agent is not particularly limited, for example, tetraalkylammoniumhalide can be mentioned. More specifically, for example, tetrabutylammoniumfluoride can be mentioned. While the solvent to be used for the aforementioned deprotection step is not particularly limited, for example, tetrahydrofuran, N-methylpyrrolidone, N,N-dimethylformamide, dimethyl sulfoxide, a mixed solvent thereof and the like can be mentioned. In addition, the byproducts such as acrylonitrile and the like to be developed in the aforementioned deprotection step may be trapped with, for example, alkylamine, thiol or a mixture thereof. Examples of the aforementioned alkylamine include alkylamine having a linear alkyl group having 1-10 carbon atoms. Examples of the aforementioned thiol include alkylthiol having a linear alkyl group having 1-10 carbon atoms. While the reaction time and reaction temperature of the aforementioned deprotection step are not particularly limited, 30 min-50 hr and 10 to 70° C. are preferable. The amount of the aforementioned deprotecting agent to be used is, for example, 10- to 1000-fold, preferably 50- to 200-fold, relative to the number of moles of the sugar (or base) in the aforementioned glycoside compound (202). The amount of the aforementioned trapping agents to be used is also the same. In addition, the method for separating and purifying the glycoside compound (209), which is the object product, from the reaction mixture of the aforementioned deprotection step is not particularly limited, and a conventional purification method can be used. Examples of the aforementioned purification method include filtration, elution, concentration, neutralization, centrifugation, chromatography (silica gel column, thin layer, reversed-phase ODS, ion exchange, gel filtration), dialysis, ultrafiltration and the like. These may be used alone or plural kinds thereof may be used in combination.

[Step A6]

A step of removing the hydroxyl-protecting group at the 5'-position of the compound (209) produced in the aforementioned step A5.

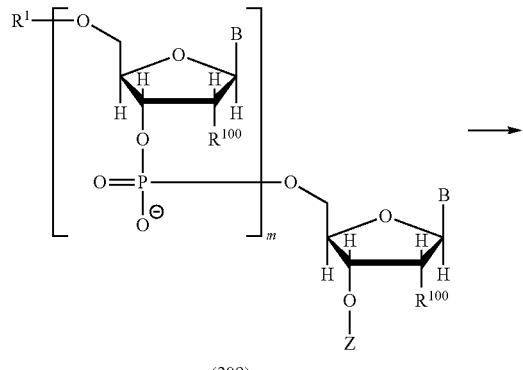

(209)

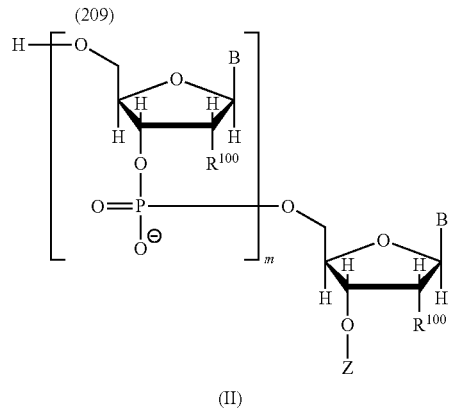

(II)

While the aforementioned acid to be used for step A6 is not particularly limited, for example, halogenated carboxylic acid, carboxylic acid and the like can be mentioned. Examples of the aforementioned halogenated carboxylic acid or carboxylic acid include trifluoroacetic acid, dichloroacetic acid, trichloroacetic acid, acetic acid and the like. The aforementioned acid may be used, for example, after dissolving in a suitable solvent. While the concentration of the solution is not particularly limited, it is, for example, 10-70 wt %. While the aforementioned solvent is not particularly limited, for example, dichloromethane, acetonitrile, chloroform, ethanol, water, buffer having pH 2-5, a mixed solvent thereof and the like can be mentioned. Examples of the aforementioned buffer include acetate buffer. While the reaction temperature in step A6 is not particularly limited, 10° C.-60° C. is preferable. While the reaction time is not particularly limited and varies depending on the kind of the acid to be used, reaction temperature and the like, it is, for example, 1 min-30 min. While the amount of the aforementioned acid to be used (number of moles) is not particularly limited, it is, for example, 1- to 200-fold, preferably 1- to 20-fold, relative to the number of moles of the sugar (or base) in the aforementioned glycoside compound (209).

The aforementioned compound (II), which is the object product of the aforementioned step A6, may be separated and purified as necessary. The "separation" includes, for example, isolation. The separation and purification method is not particularly limited and, for example, extraction, concentration, neutralization, filtration, centrifugation, reversed-phase column chromatography, ion exchange column chromatography, gel filtration column chromatography, high performance liquid chromatography, dialysis, ultrafiltration and the like can be mentioned, which may be used alone or plural kinds thereof may be used in combination.

The order of step A5 and the aforementioned step A6 may be reversed. That is, the aforementioned step A6 may be performed after the aforementioned step A4 and before the aforementioned step A5, after which the aforementioned step A5 may be performed.

Use of the nucleic acid produced by the production method of a nucleic acid of the present invention is not particularly limited and, for example, it is similar to that of known nucleic acids. Since the aforementioned nucleic acid can be produced at a low cost and with high purity when produced by the production method of a nucleic acid of the present invention, use thereof is broad and, for example, it is suitable for use in the production of a medicament and the like.

While the present invention is explained in detail in the following by referring to Examples and the like, the present invention is not limited by them.

EXAMPLES

Example 1

Synthesis of EMM Reagent (1004)

According to the following scheme E1, an EMM reagent (1004) was synthesized. "EMM" stands for "cyanoethoxymethoxymethyl" (hereinafter the same).

Scheme E1

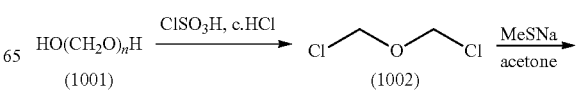

-continued

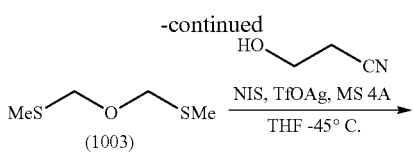

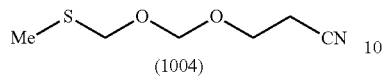

[[1] Synthesis of bis(chloromethyl)ether (1002)]

A mixture of para-formaldehyde (1001) (100 g, 3.33 mol) and concentrated hydrochloric acid (70 mL, 0.83 mol) was stirred at −5° C. to 0° C. for 30 min. Chlorosulfonic acid (190 mL, 2.86 mol) was added dropwise to the reaction mixture over 4 hr. The mixture was further stirred at −5° C. to 0° C. for 3 hr and further at room temperature overnight. The upper layer of the reaction mixture was separated using a partitioning funnel and washed with ice water. The reaction mixture after washing was added into an Erlenmeyer flask containing ice, and cooled in an ice bath. While vigorously stirring the solution, 40% aqueous sodium hydroxide solution was slowly added until the aqueous layer became strong alkali (pH 11). The resultant product was separated by a partitioning funnel, and dried by adding potassium carbonate and potassium hydroxide in an ice bath. The desiccant was removed by filtration to give the object compound (1002) as a colorless oil (158 g, yield 83%). Reference was made to Saul R. Buc, Org. Synth., Coll. Vol. 4, p. 101 (1963); Vol. 36, p. 1 (1956) for the operation for the synthesis. The instrumental analysis value of the compound (1002) is shown below.

Compound (1002):

$^1$H-NMR (400 MHz, CDCl$_3$) δ: 5.55(4H, s).

[[2] Synthesis of bis(methylthiomethyl)ether (1003)]

Methylthiosodium.4.5 hydrate (330 g, 2.17 mol) was added to a solution of bis(chloromethyl)ether (1002) (50 g, 0.43 mol) in acetone (720 ml), and the mixture was vigorously stirred at room temperature for 1 hr. The reaction solution was filtered through celite, and the filtrate was concentrated under reduced pressure. Dichloromethane was added, and the mixture was washed three times with saturated aqueous sodium hydrogen carbonate solution and once with saturated aqueous sodium chloride solution. The organic layer was dried over anhydrous sodium sulfate and concentrated under reduced pressure. The crude product was evaporated under reduced pressure (70-84° C., 20-22 mmHg (2.7-2.9 kPa)) to give the object compound (1003) as a colorless oil (43.7 g, yield 74%). This synthesis method is an improved synthesis method of the synthesis method described in Eur. Pat. Appl. (1994), EP604910A1 to further improve the yield of the object compound (yield 48% described in the aforementioned document). The instrumental analysis value of the compound (1003) is shown below.

Compound (1003):

$^1$H-NMR (400 MHz, CDCl$_3$) δ: 4.77(4H, s), 2.16(6H, s).

[[3] Synthesis of EMM Reagent (1004)]

Bis(methylthiomethyl)ether (1003) (10.0 g, 72 mmol) was dissolved in tetrahydrofuran (100 ml) under an argon atmosphere. Cyanoethanol (2.6 g, 36 mmol) and molecular sieves 4A (10 g) were added to the solution, and the mixture was stirred for 10 min. N-iodosuccinimide (9.8 g, 43 mmol) was further added and dissolved in the mixture, and the mixture was cooled to 0° C. After cooling, trifluoromethanesulfone acid silver (0.28 g, 1.1 mmol) was added, and the mixture was stirred for 1 hr. After stirring, ethyl acetate was added, and the mixture was washed with saturated aqueous sodium thiosulfate solution, saturated aqueous sodium hydrogen carbonate solution and saturated aqueous sodium chloride solution in this order. Thereafter, the organic layer was separated, dried over anhydrous sodium sulfate, and concentrated under reduced pressure. The crude product was purified by silica gel column chromatography (hexane:ethyl acetate=4:1) to give the object compound (1004) as a colorless oil (3.4 g, yield 58%). The instrumental analysis value of the compound (1004) is shown below.

Compound (1004):

$^1$H-NMR (400 MHz, CDCl$_3$) δ: 4.86(2H, s), 4.73(2H, s), 3.80(2H, t, J=6.3 Hz), 2.64(2H, t, J=6.3 Hz), 2.18(3H, s).

GC-MS (EI+): m/z 161[M]$^+$, 84[CH$_2$O(CH$_2$)$_2$CN]$^+$, 61[CH$_3$SCH$_2$]$^+$, 54[(CH$_2$)$_2$CN]$^+$

Example 2

Synthesis of Uridine EMM Amidite (1009)

According to the following scheme E2, uridine EMM amidite (1009) was synthesized.

Scheme E2

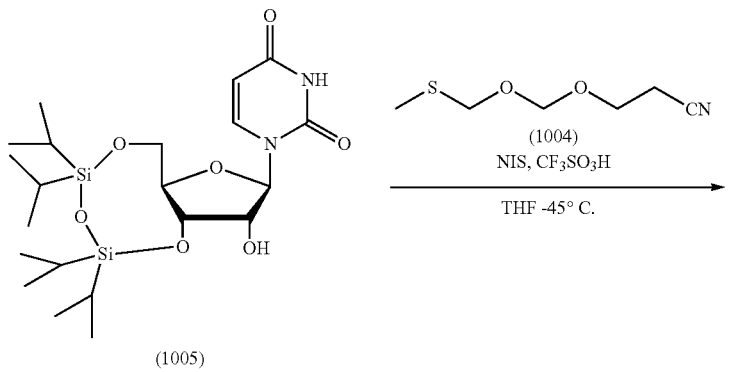

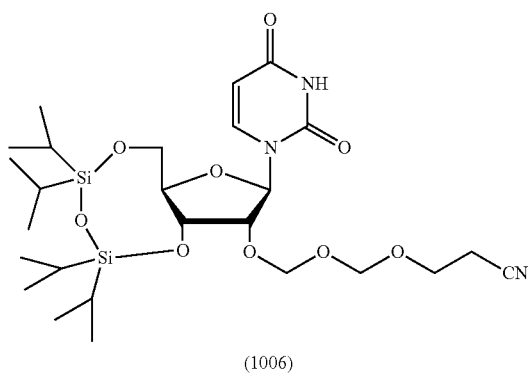

(1006)

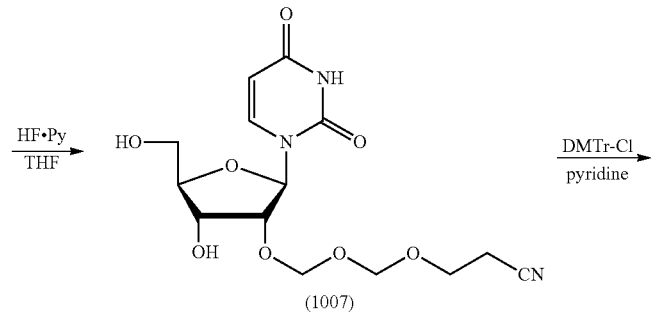

(1007)

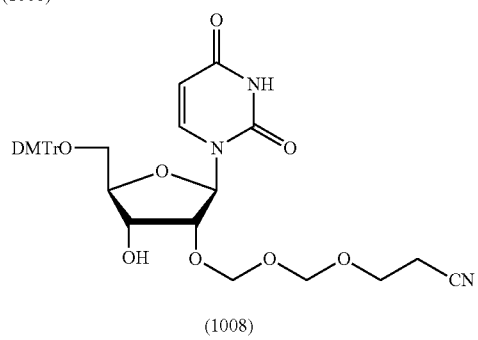

(1008)

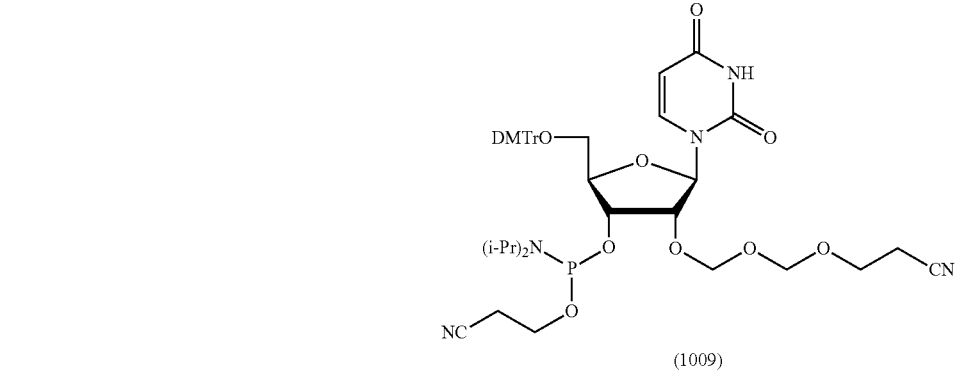

(1009)

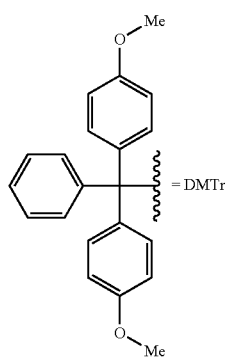 [SMILES: *C(c1ccccc1)(c1ccc(OC)cc1)c1ccc(OC)cc1]

= DMTr

[[1] Synthesis of 3',5'-O-(tetraisopropyldisiloxane-1,3-diyl)-2'-O-(2-cyanoethoxymethoxymethyl)uridine (1006)]

3',5'-O-(Tetraisopropyldisiloxane-1,3-diyl)uridine (1005) (0.50 g, 1.0 mmol) was dissolved in tetrahydrofuran (5 mL) under an argon atmosphere, the EMM reagent (1004) (0.26 g, 1.6 mmol) was further added, and the mixture was stirred. After cooling this to −45° C., trifluoromethanesulfonic acid (0.24 g, 1.6 mmol) was added, and the mixture was stirred for 10 min. After stirring, N-iodosuccinimide (0.36 g, 1.6 mmol) was added, and the mixture was further stirred for 5 hr. After completion of the reaction, triethylamine was added to quench the reaction. Ethyl acetate was further added, and the mixture was washed twice with saturated aqueous sodium thiosulfate solution and once with saturated aqueous sodium chloride solution. The organic layer was dried over anhydrous sodium sulfate and concentrated under reduced pressure. Ethyl acetate was added to the residue, and the mixture was washed once with saturated aqueous sodium thiosulfate solution and once with saturated aqueous sodium chloride solution. The organic layer was dried over anhydrous sodium sulfate and concentrated under reduced pressure. The obtained crude product was purified by silica gel column chromatography (ethyl acetate:hexane=1:1) to give the object compound (1006) (0.51 g, yield 83%). The instrumental analysis value of the compound (1006) is shown below.

Compound (1006):

$^1$H-NMR (400 MHz, CDCl$_3$) δ: 8.41(1H, s), 7.90(1H, d, J=7.8 Hz), 5.72(1H, s), 5.67 (1H, d, J=8.3 Hz), 5.15-5.08 (2H, m), 4.98(1H, d, J=6.8 Hz), 4.84(1H, d, J=4.4 Hz), 4.26-4.11(4H, m), 4.04-3.97(2H, m), 3.90-3.78(1H, m), 2.70-2.65(2H, m), 1.11-0.94(28H, m).

[[2] Synthesis of 2'-O-(2-cyanoethoxymethoxymethyl)uridine (1007)]

3',5'-O-(Tetraisopropyldisiloxane-1,3-diyl)-2'-O-(2-cyanoethoxymethoxymethyl)uridine (1006) (3.8 g, 6.3 mmol) was dissolved in tetrahydrofuran (15 mL), hydrogen fluoride pyridine (1.6 g, 16 mmol) was further added, and the mixture was stirred at room temperature overnight. The obtained precipitate was collected by filtration and dried under reduced pressure to give the aforementioned precipitate (1.6 g). On the other hand, toluene was added to the residual filtrate and the supernatant was removed by decantation. To the solution after removal of the supernatant was added diisopropylether, the supernatant was removed by decantation, and this operation was repeated until crystals were obtained. The obtained precipitate (crystal) was collected by filtration and dried under reduced pressure to give the aforementioned precipitate (crystal) (0.5 g). The respective aforementioned precipitates were combined to give the object compound (1007) (2.1 g, yield 92%). The instrumental analysis value of the compound (1007) is shown below.

Compound (1007):

$^1$H-NMR (400 MHz, CDCl$_3$) δ: 10.23(1H, br.s), 7.90(1H, d, J=7.8 Hz), 5.84(1H, d, J=2.9 Hz), 5.59(1H, d, J=8.3 Hz), 5.09(1H, d, J=7.0 Hz), 4.98(1H, d, J=6.7 Hz), 4.87(2H, s), 4.25-4.22(3H, m), 3.99(1H, s), 3.83-3.69(5H, m), 2.70-2.61 (2H, m).

[[3] Synthesis of 5'-O-(4,4'-dimethoxytrityl)-2'-O-(2-cyanoethoxymethoxymethyl)uridine (1008)]

2'-O-(2-Cyanoethoxymethoxymethyl)uridine (1007) (2.1 g, 6.0 mmol) was azeotropically distilled with pyridine, and the solvent was evaporated by a vacuum pump. This operation was performed three times. Thereafter, 4,4'-dimethoxytrityl chloride (2.6 g, 7.2 mmol) and pyridine (10 mL) were added, and the mixture was stirred for 2 hr. After stirring, dichloromethane was added, and the mixture was washed twice with saturated aqueous sodium hydrogen carbonate solution and successively once with saturated aqueous sodium chloride solution. The organic layer was dried over anhydrous sodium sulfate and concentrated under reduced pressure. The obtained crude product was purified by silica gel column chromatography (acetone:hexane=3:7, containing 0.05% pyridine→dichloromethane:methanol=9:1, containing 0.05% pyridine) to give the object compound (1008) (3.8 g, yield 96%). The instrumental analysis value of the compound (1008) is shown below.

Compound (1008):

$^1$H-NMR (400 MHz, CDCl$_3$) δ: 8.62(1H, br.s), 7.99(1H, d, J=7.8 Hz), 7.40-7.25(9H, m), 6.90-6.84(4H, m), 5.96(1H, d, J=2.0 Hz), 5.28(1H, d, J=8.3 Hz), 5.18(1H, d, J=6.8 Hz), 5.03(1H, d, J=7.3 Hz), 4.87(2H, d, J=7.3 Hz), 4.48(1H, q, J=5.4 Hz), 4.29(1H, dd, J=5.1, 2.2 Hz), 4.11-4.07(1H, m), 3.87(2H, t, J=6.0 Hz), 3.84(6H, s), 3.55(2H, dd, J=9.0, 2.2 Hz), 2.76(1H, d, J=7.8 Hz), 2.65(2H, t, J=6.6 Hz).

[[4] Synthesis of 5'-O-(4,4'-dimethoxytrityl)-2'-O-(2-cyanoethoxymethoxymethyl)uridine 3'-O-(2-cyanoethyl N,N-diisopropylphosphoramidite) (1009)]

5'-O-(4,4'-Dimethoxytrityl)-2'-O-(2-cyanoethoxymethoxymethyl)uridine (1008) (3.7 g, 5.6 mmol) was azeotropically distilled with pyridine, and the solvent was evaporated by a vacuum pump. This operation was performed three times. Furthermore, under an argon atmosphere, diisopropylammonium tetrazolide (1.2 g, 6.8 mmol) and acetonitrile (10 mL) were added. 2-Cyanoethyl-N,N,N',N'-tetraisopropylphosphorodiamidite (2.0 g, 6.8 mmol) dissolved in acetonitrile (20 mL) was added to the reaction solution, and the mixture was stirred at 45° C. for 2 hr. Furthermore, dichloromethane was added, and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (acetone:hexane=1:1, containing 0.05% pyridine) to give the object compound (1009) (4.3 g, yield 89%). The instrumental analysis value of the compound (1009) is shown below.

Compound (1009):

$^{31}$P-NMR (162 MHz, CDCl$_3$) δ: 153.5, 151.9.

MS (FAB+): m/z 882[M+Na]$^+$

Example 3

Synthesis of Cytidine EMM Amidite (1014)

According to the following scheme E3, cytidine EMM amidite (1014) was synthesized.

Scheme E3

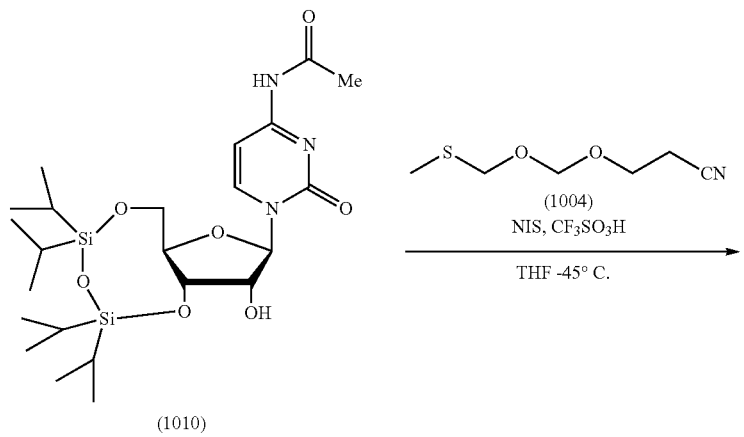

51 52
-continued
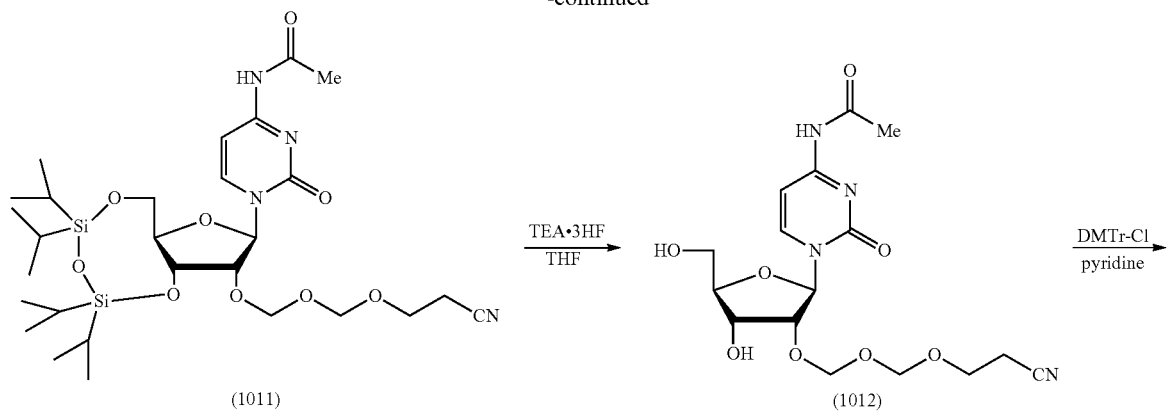
(1011) → (1012)
TEA·3HF / THF, then DMTr-Cl / pyridine
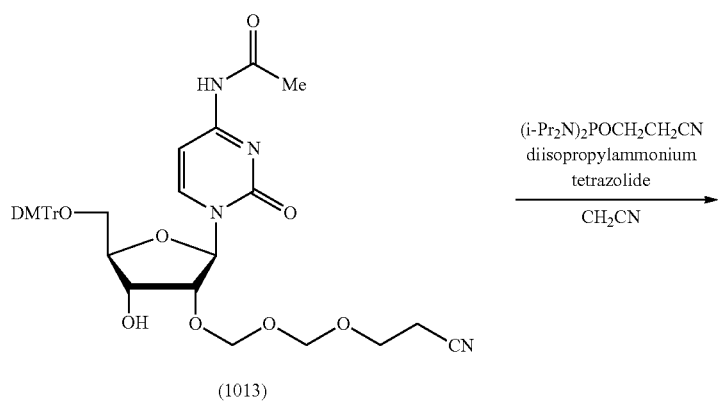
(1013)
(i-Pr₂N)₂POCH₂CH₂CN
diisopropylammonium tetrazolide
─────────────→
CH₃CN
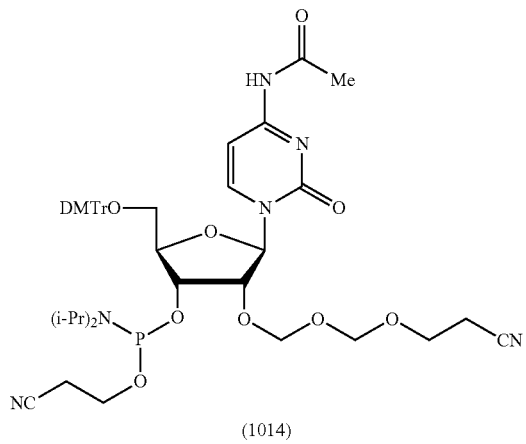
(1014)
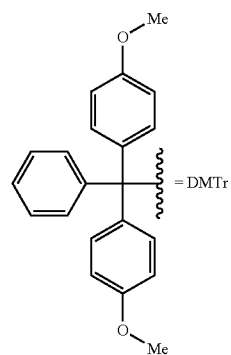
= DMTr

[[1] Synthesis of $N^4$-acetyl-3',5'-O-(tetraisopropyldisiloxane-1,3-diyl)-2'-O-(2-cyanoethoxymethoxymethyl)cytidine (1011)]

$N^4$-Acetyl-3',5'-O-(tetraisopropyldisiloxane-1,3-diyl)cytidine (1010) (3.0 g, 5.7 mmol) was azeotropically distilled with toluene, and the solvent was evaporated by a vacuum pump. This operation was performed three times. The thus-obtained mixture was dissolved in tetrahydrofuran (30 mL) under an argon atmosphere, the EMM reagent (1004) (2.8 g, 18 mmol) was added, and the mixture was stirred. The mixture was cooled to −45° C., trifluoromethane sulfonic acid (1.3 g, 8.8 mmol) was added, and the mixture was stirred for 10 min. Furthermore, N-iodosuccinimide (2.0 g, 9.0 mmol) was added, and the mixture was stirred for 5 hr. After completion of the reaction, triethylamine was added to quench the reaction. Furthermore, ethyl acetate was added, and the mixture was washed twice with saturated aqueous sodium thiosulfate solution and once with saturated aqueous sodium chloride solution. The organic layer after washing was dried over anhydrous sodium sulfate and concentrated under reduced pressure. Ethyl acetate was added to the obtained residue, and the mixture was washed once with saturated aqueous sodium thiosulfate solution and once with saturated aqueous sodium chloride solution. The organic layer after washing was dried over anhydrous sodium sulfate and concentrated under reduced pressure to give the object compound (1011) (5.3 g, crude product). The instrumental analysis value of the compound (1011) is shown below.

Compound (1011):

$^1$H-NMR (400 MHz, CDCl$_3$) δ: 9.17(1H, s), 8.30(1H, d, J=7.2 Hz), 7.41(1H, d, J=7.8 Hz), 5.79(1H, s), 5.18(1H, d, J=6.8 Hz), 5.03(d, 1H, J=7.4 Hz), 4.29(1H, d, J=13.7 Hz), 4.23-4.10(5H, m), 4.03-3.96(2H, m), 3.87-3.75(1H, m), 2.76-2.65(2H, m), 2.24(3H, s), 1.11-0.89(28H, m).

[[2] Synthesis of $N^4$-acetyl-2'-O-(2-cyanoethoxymethoxymethyl)cytidine (1012)]

$N^4$-Acetyl-3',5'-O-(tetraisopropyldisiloxane-1,3-diyl)-2'-O-(2-cyanoethoxymethoxymethyl)cytidine (1011) (5.2 g, 8.1 mmol) was dissolved in tetrahydrofuran (30 mL) under an argon atmosphere. To the solution was added triethylaminehydrogen trifluoride (1.6 g, 9.7 mmol), and the mixture was stirred at 45° C. for 1 hr. After stirring, the mixture was allowed to cool to room temperature, and the precipitated sediment was collected by filtration. The sediment was washed with tetrahydrofuran and dried under reduced pressure to give the object compound (1012) (1.5 g, yield 68%). The instrumental analysis value of the compound (1012) is shown below.

Compound (1012):

$^1$H-NMR (400 MHz, D$_2$O) δ: 8.24(1H, d, J=7.3 Hz), 7.24(1H, d, J=7.8 Hz), 5.92(1H, d, J=2.4 Hz), 5.02(1H, d, J=6.8 Hz), 4.89(1H, d, J=6.8 Hz), 4.79-4.74(2H, m), 4.29 (1H, dd, J=4.9, 2.9 Hz), 4.17(1H, t, J=6.3 Hz), 4.09-4.05 (1.0H, m), 3.90-3.85(1H, m), 3.77-3.70(3H, m), 2.67(2H, t, J=6.1 Hz), 2.12(3H, s).

[[3] Synthesis of $N^4$-acetyl-5'-O-(4,4'-dimethoxytrityl)-2'-O-(2-cyanoethoxymethoxymethyl)cytidine (1013)]

$N^4$-Acetyl-2'-O-(2-cyanoethoxymethoxymethyl) cytidine (1012) (0.70 g, 1.8 mmol) was azeotropically distilled with pyridine, and the solvent was evaporated by a vacuum pump. This operation was performed three times. Furthermore, 4,4'-dimethoxytrityl chloride (0.91 g, 2.7 mmol) and pyridine (10 mL) were added, and the mixture was stirred for 4 hr. After completion of the reaction, methanol was added, and the mixture was concentrated under reduced pressure. Dichloromethane was added to the residue and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate:acetone:hexane=1:1:1, containing 0.05% pyridine→1:1:0, containing 0.05% pyridine) to give the object compound (1013) (1.1 g, yield 87%). The instrumental analysis value of the compound (1013) is shown below.

Compound (1013):

$^1$H-NMR (400 MHz, CDCl$_3$) δ: 8.61(1H, br.s), 8.49(1H, d, J=7.8 Hz), 7.42-7.26(9H, m), 7.09(1H, d, J=7.3 Hz), 6.88-6.86(4H, m), 5.94(1H, s), 5.35(1H, d, J=6.8 Hz), 5.11 (1H, d, J=6.8 Hz), 4.92(1H, d, J=7.3 Hz), 4.87(1H, d, J=7.3 Hz), 4.49-4.40(1H, m), 4.29(1H, d, J=4.9 Hz), 4.15-4.08 (1H, m), 3.86(t, 2H, J=6.2 Hz), 3.82(s, 6H), 3.63(dd, 1H, J=10.6, 2.6 Hz), 3.55(dd, 1H, J=10.6, 2.6 Hz), 2.64(2H, t, J=6.3 Hz), 2.56(d, 1H, J=8.8 Hz), 2.21(3H, s).

[[4] Synthesis of $N^4$-acetyl-5'-O-(4,4'-dimethoxytrityl)-2'-O-(2-cyanoethoxymethoxymethyl)cytidine 3'-O-(2-cyanoethyl N,N-diisopropylphosphoramidite) (1014)]

$N^4$-Acetyl-5'-O-(4,4'-dimethoxytrityl)-2'-O-(2-cyanoethoxymethoxymethyl)cytidine (1013) (1.0 g, 1.4 mmol) was azeotropically distilled with acetonitrile, and the solvent was evaporated by a vacuum pump. This operation was performed three times. Furthermore, under an argon atmosphere, diisopropylammonium tetrazolide (0.27 g, 1.6 mmol) and acetonitrile (4 mL) were added. 2-Cyanoethyl-N,N,N',N'-tetraisopropyl phosphorodiamidite (0.63 g, 2.1 mmol) dissolved in acetonitrile (1.5 mL) was added to the reaction solution, and the mixture was stirred at 45° C. for 3 hr. After stirring, dichloromethane was added, and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (acetone:hexane:isopropyl acetate=1:2:1, containing 0.1% triethylamine→acetone:hexane:ethyl acetate=1:1:1, containing 0.1% triethylamine) to give the object compound (1014) (0.9 g, yield 71%). The instrumental analysis value of the compound (1014) is shown below.

Compound (1014):

$^{31}$P-NMR (162 MHz, CDCl$_3$) δ: 153.6, 151.5.

MS (FAB+): m/z 923[M+Na]$^+$

Example 4

Synthesis of Adenosine EMM Amidite (1019)

According to the following scheme E4, adenosine EMM amidite (1019) was synthesized.

Scheme E4
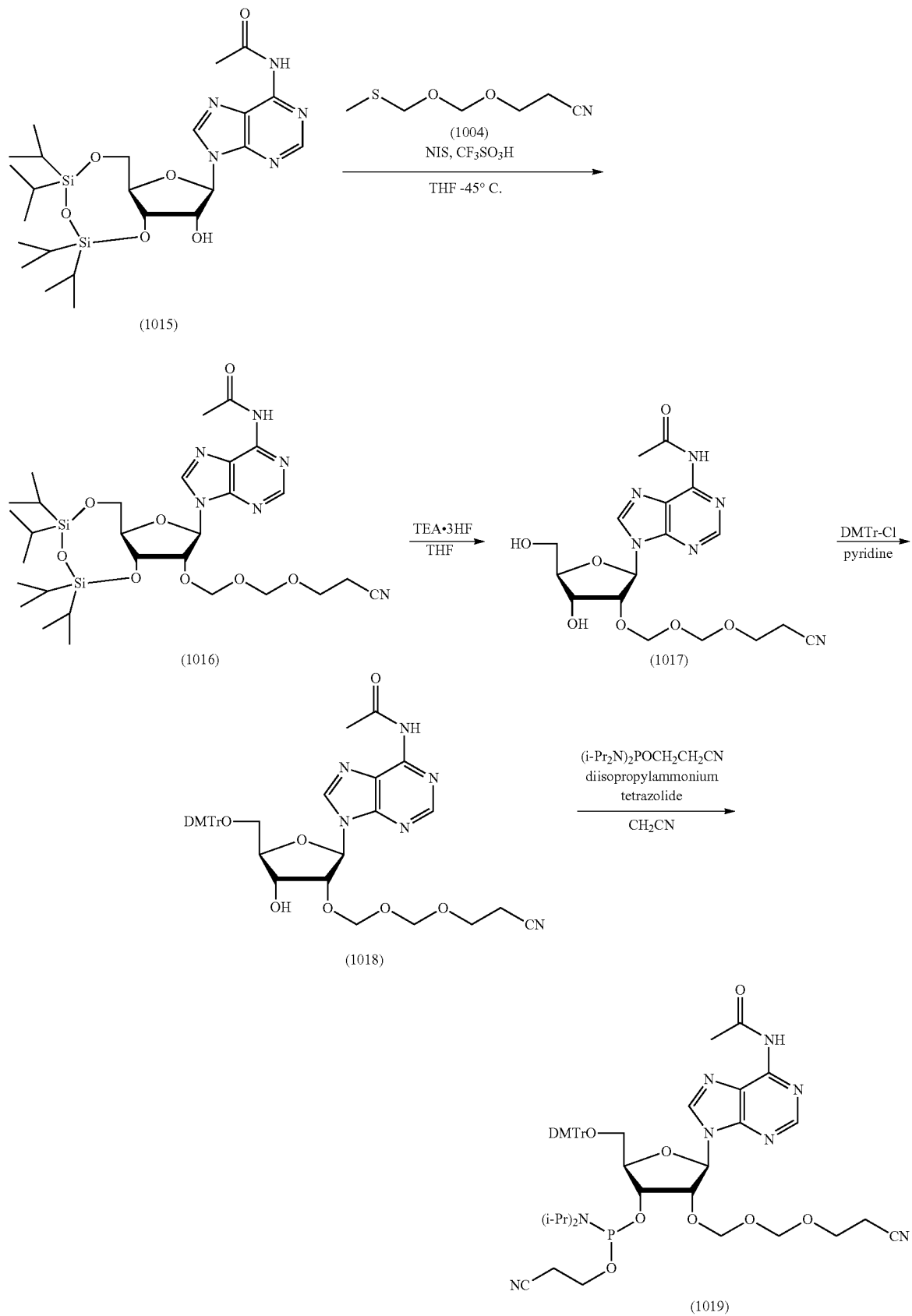

[[1] Synthesis of N[6]-acetyl-3',5'-O-(tetraisopropyldisiloxane-1,3-diyl)-2'-O-(2-cyanoethoxymethoxymethyl)adenosine (1016)]

Toluene was added to N[6]-acetyl-3',5'-O-(tetraisopropyldisiloxane-1,3-diyl)adenosine (1015) (3.0 g, 5.4 mmol), and the solvent was evaporated by a vacuum pump. This operation was performed three times, and water was azeotropically distilled away. The thus-obtained mixture was dissolved in tetrahydrofuran (30 mL) under an argon atmosphere, the EMM reagent (1004) (2.6 g, 16 mmol) was added, and the mixture was stirred and cooled to −45° C. Trifluoromethanesulfonic acid (2.4 g, 16 mmol) was added, and the mixture was stirred for 10 min. After stirring, N-iodosuccinimide (3.7 g, 16 mmol) was added, and the mixture was stirred for 5 hr. After completion of the reaction, triethylamine was added to quench the reaction. Furthermore, ethyl acetate was added, and the mixture was washed twice with saturated aqueous sodium thiosulfate solution, twice with saturated aqueous sodium hydrogen carbonate solution, and once with saturated aqueous sodium chloride solution. The organic layer was dried over anhydrous sodium sulfate and concentrated under reduced pressure. Ethyl acetate was added to the residue, and the mixture was washed once with saturated aqueous sodium thiosulfate solution and once with saturated aqueous sodium chloride solution. The organic layer was dried over anhydrous sodium sulfate and concentrated under reduced pressure to give the object compound (1016) (8.6 g, crude product). The instrumental analysis value of the compound (1016) is shown below.

Compound (1016):

$^1$H-NMR (400 MHz, CDCl$_3$) δ: 8.68(1H, s), 8.66(1H, s), 8.33(1H, s), 6.12(1H, s), 5.08(1H, d, J=7.0 Hz), 4.91-4.80 (3H, m), 4.67(1H, d, J=7.8 Hz), 4.52(1H, d, J=4.3 Hz), 4.25(1H, d, J=13.0 Hz), 4.17(1H, d, J=9.4 Hz), 4.09-4.02 (2H, m), 3.89-3.80(1H, m), 2.67(2H, m), 2.63(3H, s), 1.11-0.98(28H, m).

[[2] Synthesis of N[6]-acetyl-2'-O-(2-cyanoethoxymethoxymethyl)adenosine (1017)]

N[6]-Acetyl-3',5'-O-(tetraisopropyldisiloxane-1,3-diyl)-2'-O-(2-cyanoethoxymethoxymethyl)adenosine (1016) (8.2 g, 13 mmol) was dissolved in tetrahydrofuran (40 mL) under an argon atmosphere. Triethylamine hydrogen trifluoride (2.4 g, 15 mmol) was added to the solution, and the mixture was stirred at 45° C. for 2 hr. The mixture was allowed to cool to room temperature, and the precipitated sediment was collected by filtration. The sediment was washed with tetrahydrofuran and dried under reduced pressure to give the object compound (1017) (1.2 g, yield 52%) from the primary crystals alone. The instrumental analysis value of the compound (1017) is shown below.

Compound (1017):

$^1$H-NMR (400 MHz, DMSO-d$_6$) δ: 10.71(1H, s), 8.71 (1H, s), 8.66(1H, s), 6.17(1H, d, J=5.8 Hz), 5.41(1H, d, J=5.4 Hz), 5.20(2H, m), 4.80-4.73(3H, m), 4.65-4.60(2H, m), 4.37-4.33(1H, m), 4.00-4.01(1H, m), 3.73-3.64(1H, m), 3.61-3.51(2H, m), 2.79-2.64(2H, m), 2.22(3H, s).

[[3] Synthesis of N[6]-acetyl-5'-O-(4,4'-dimethoxytrityl)-2'-O-(2-cyanoethoxymethoxymethyl)adenosine (1018)]

N[6]-Acetyl-2'-O-(2-cyanoethoxymethoxymethyl) adenosine (1017) (1.0 g, 2.4 mmol) was azeotropically distilled with pyridine, and the solvent was evaporated by a vacuum pump. This operation was performed three times. Thereafter, 4,4'-dimethoxytrityl chloride (0.96 g, 2.8 mmol) and pyridine (10 mL) were added, and the mixture was stirred for 3 hr. After completion of the reaction, methanol was added, the mixture was concentrated under reduced pressure, and dichloromethane was added to the residue. The obtained solution was washed twice with saturated aqueous sodium hydrogen carbonate solution and once with saturated aqueous sodium chloride solution. The organic layer was dried over anhydrous sodium sulfate and concentrated under reduced pressure. The obtained crude product was purified by silica gel column chromatography (acetone:hexane:ethyl acetate=1:2:2, containing 0.05% pyridine→1:1:1, containing 0.05% pyridine) to give the object compound (1018) (1.3 g, yield 76%). The instrumental analysis value of the compound (1018) is shown below.

Compound (1018):

$^1$H-NMR (400 MHz, CDCl$_3$) δ: 8.62-8.58(2H, m), 8.17 (1H, s), 7.46-7.39(2H, m), 7.37-7.20(7H, m), 6.87-6.79(4H, m), 6.20(1H, d, J=4.9 Hz), 5.03-4.75(3H, m), 4.52(1H, s), 4.30-4.23(1H, m), 4.12(2H, d, J=7.3 Hz), 3.79(6H, s), 3.79-3.69(2H, m), 3.52-3.44(2H, m), 2.61(3H, s), 2.58(1H, d, J=5.5 Hz), 2.51(2H, t, J=5.9 Hz).

[[4] Synthesis of N[6]-acetyl-5'-O-(4,4'-dimethoxytrityl)-2'-O-(2-cyanoethoxymethoxymethyl)adenosine 3'-O-(2-cyanoethyl N, N-diisopropylphosphoramidite) (1019)]

N[6]-Acetyl-5'-O-(4,4'-dimethoxytrityl)-2'-O-(2-cyanoethoxymethoxymethyl)adenosine (1018) (1.0 g, 1.4 mmol) was azeotropically distilled with pyridine, and the solvent was evaporated by a vacuum pump. This operation was performed three times. Furthermore, under an argon atmosphere, diisopropylammonium tetrazolide (0.31 g, 1.8 mmol) and acetonitrile (3 mL) were added. 2-Cyanoethyl-N,N,N',N'-tetraisopropyl phosphorodiamidite (0.54 g, 1.8 mmol) dissolved in acetonitrile (1 mL) was added to the reaction solution, and the mixture was stirred at 40° C. for 4 hr. Furthermore, dichloromethane was added, and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (acetone:hexane:ethyl acetate=2:2:1, containing 0.1% triethylamine) to give the object compound (1019) (1.1 g, yield 73%). The instrumental analysis value of the compound (1019) is shown below.

Compound (1019):

$^{31}$P-NMR (162 MHz, CDCl$_3$) δ: 152.7, 152.6.

MS (FAB+): m/z 947[M+Na]$^+$, 925[M+H]$^+$

Example 5

Synthesis of Guanosine EMM Amidite (1024)

According to the following scheme E5, guanosine EMM amidite (1024) was synthesized.

Scheme E5
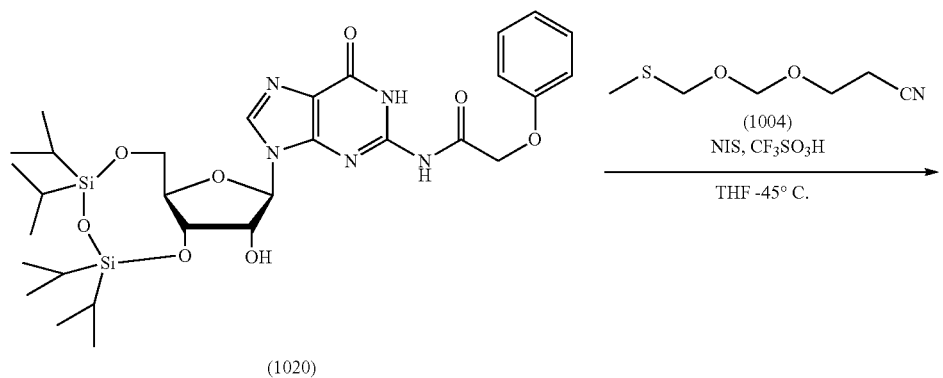
(1020)
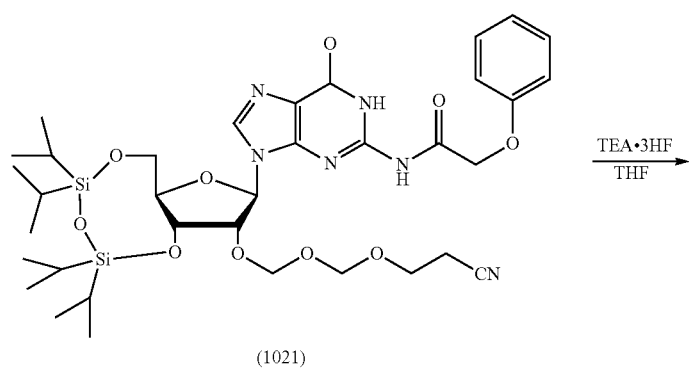
(1021)
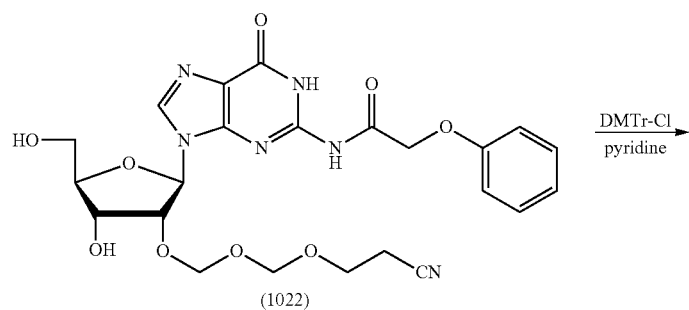
(1022)
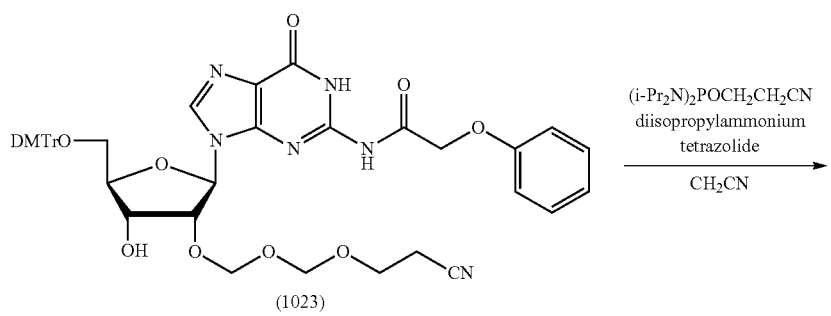
(1023)

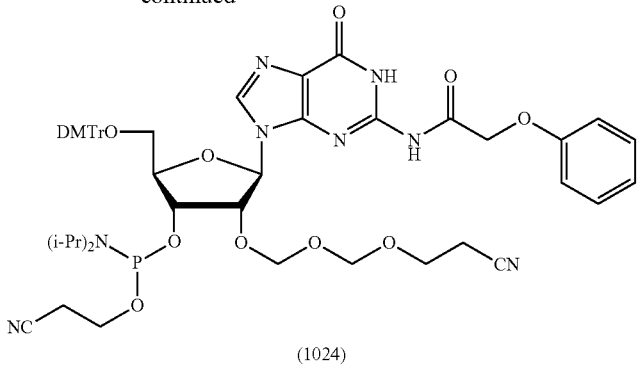

(1024)

[[1] Synthesis of N²-phenoxyacetyl-3',5'-O-(tetraisopropyl-disiloxane-1,3-diyl)-2'-O-(2-cyanoethoxymethoxymethyl) guanosine (1021)]

N²-Phenoxyacetyl-3',5'-O-(tetraisopropyldisiloxane-1,3-diyl)guanosine (1020) (3.5 g, 5.3 mmol) was dissolved in tetrahydrofuran, toluene was added, and the solvent was evaporated by a vacuum pump. This operation was performed three times, and water was azeotropically distilled away. The thus-obtained mixture was dissolved in tetrahydrofuran (30 mL) under an argon atmosphere, and the EMM reagent (1004) (2.6 g, 16 mmol) was added. The mixture was stirred and cooled to −45° C., trifluoromethanesulfonic acid (2.4 g, 16 mmol) was added, and the mixture was stirred for 10 min. Thereafter, N-iodosuccinimide (3.6 g, 16 mmol) was added, and the mixture was further stirred for 5 hr. After completion of the reaction, triethylamine was added to quench the reaction. Furthermore, ethyl acetate was added, and the mixture was washed twice with saturated aqueous sodium thiosulfate solution, twice with saturated aqueous sodium hydrogen carbonate solution, and once with saturated aqueous sodium chloride solution. The organic layer after washing was dried over anhydrous sodium sulfate and concentrated under reduced pressure. Ethyl acetate was added to the obtained residue, and the mixture was washed once with saturated aqueous sodium thiosulfate solution and once with saturated aqueous sodium chloride solution. The organic layer was dried over anhydrous sodium sulfate and concentrated under reduced pressure to give the object compound (1021) (8.2 g, crude product). The instrumental analysis value of the compound (1021) is shown below.

Compound (1021):

¹H-NMR (400 MHz, CDCl₃) δ: 11.79(1H, s), 9.11(1H, s), 8.04(1H, s), 7.41-7.34(2H, m), 7.13-6.97(3H, m), 5.94(1H, s), 5.08, 4.97(2H, 2d, J=7.2 Hz), 4.87-4.67(2H, m), 4.51-4.46(1H, dd, J=9.3, 4.9 Hz), 4.33-4.24(2H, m), 4.15(1H, d, J=9.3 Hz), 4.02(1H, dd, J=13.2, 2.4 Hz), 3.77-3.71(2H, m), 2.76-2.53(2H, m), 1.11-0.94(28H, m).

[[2] Synthesis of N²-phenoxyacetyl-2'-O-(2-cyanoethoxymethoxymethyl)guanosine (1022)]

N²-Phenoxyacetyl-3',5'-O-(tetraisopropyldisiloxane-1,3-diyl)-2'-O-(2-cyanoethoxymethoxymethyl)guanosine (1021) (8.0 g, 10 mmol) was dissolved in tetrahydrofuran (40 mL) under an argon atmosphere. Triethylamine hydrogen trifluoride (2.0 g, 12 mmol) was added, and the mixture was stirred at 35° C. for 2 hr. Toluene was added to the filtrate, and the mixture was decanted. Diethylether was added, and the mixture was decanted. This operation was repeated until crystals were obtained. The precipitate was collected by filtration and dried under reduced pressure to give the object compound (1022) (0.90 g, yield 38%) from the primary crystals alone. The instrumental analysis value of the compound (1022) is shown below.

Compound (1022):

¹H-NMR (400 MHz, DMSO-d₆) δ: 11.78(2H, br.s), 8.32 (1H, s), 7.41-7.31(2H, m), 7.07-6.98(3H, m), 6.00(1H, d, J=5.8 Hz), 5.37(1H, s), 5.18(1H, s), 4.88(2H, s), 4.85-4.78 (2H, m), 4.72-4.59(3H, m), 4.34(1H, m), 4.00(1H, m), 3.75-3.56(3H, m), 2.79-2.69(2H, m).

[[3] Synthesis of N²-phenoxyacetyl-5'-O-(4,4'-dimethoxytrityl)-2'-O-(2-cyanoethoxymethoxymethyl)guanosine (1023)]

N²-Phenoxyacetyl-2'-O-(2-cyanoethoxymethoxymethyl)guanosine (1022) (0.70 g, 1.3 mmol) was azeotropically distilled with pyridine, and the solvent was evaporated by a vacuum pump. This operation was performed three times. The thus-obtained mixture was dissolved in pyridine (7 mL) and tetrahydrofuran (7 mL) under an argon atmosphere, molecular sieves 4A was added, and the mixture was stirred for 10 min. Thereafter, 4,4'-dimethoxytrityl chloride (0.54 g, 1.6 mmol) was added, and the mixture was further stirred for 4 hr. After completion of the reaction, dichloromethane was added, and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (dichloromethane:acetonitrile:methanol=300:100:8, containing 0.05% pyridine) to give the object compound (1023) (0.80 g, yield 73%). The instrumental analysis value of the compound (1023) is shown below.

Compound (1023):

¹H-NMR (400 MHz, CDCl₃) δ: 11.82(1H, s), 8.63(1H, s), 7.84(1H, s), 7.43-7.21(9H, m), 6.86-6.82(4H, m), 6.06(1H, d, J=5.9 Hz), 4.95(1H, t, J=5.7 Hz), 4.78(2H, m), 4.67-4.63 (2H, m), 4.50-4.45(1H, m), 4.30-4.26(1H, m), 3.81(6H, s), 3.79-3.67(2H, m), 3.44(2H, dd, J=10.6, 3.7 Hz), 2.91(1H, s), 2.64-2.56(2H, m), 1.66(3H, s).

[[4] Synthesis of 5N²-phenoxyacetyl-5'-O-(4,4'-dimethoxytrityl)-2'-O-(2-cyanoethoxymethoxymethyl)guanosine 3'-O-(2-cyanoethyl N, N-diisopropylphosphoramidite) (1024)]

N²-Phenoxyacetyl-5'-O-(4,4'-dimethoxytrityl)-2'-O-(2-cyanoethoxymethoxymethyl)guanosine (1023) (0.70 g, 0.84 mmol) was azeotropically distilled with pyridine, and the solvent was evaporated by a vacuum pump. This operation was performed three times. To the thus-obtained mixture were added diisopropylammonium tetrazolide (0.16 g, 0.92 mmol) and acetonitrile (2 mL) under an argon atmosphere. 2-Cyanoethyl-N,N,N',N'-tetraisopropyl phosphorodiamidite (0.51 g, 1.7 mmol) dissolved in acetonitrile (1 mL) was added to the reaction solution, and the mixture was stirred at 40° C. for 5 hr. After stirring, dichloromethane was added, and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate:acetonitrile=40:1, containing 0.1% triethylamine) to give the object compound (1024) (0.56 g, yield 65%). The instrumental analysis value of the compound (1024) is shown below.

Compound (1024):
$^{31}$P-NMR (162 MHz, CDCl$_3$) δ: 152.7, 152.6.
MS (FAB+): m/z 1055[M+Na]$^+$, 1033[M+H]$^+$ Example 6

Synthesis of Uridine 40-Mer (U40mer) Using Uridine EMM Amidite (1009)

Using the uridine EMM amidite (1009) synthesized in Example 2 and a nucleic acid automatic synthesizer (Expedite 8909 DNA/RNA synthesizer: trade name of Applied Biosystems), an uridine 40-mer shown by the sequence of the following SEQ ID NO: 1 was synthesized.

(SEQ ID NO: 1)
5'-UUUUUUUUUUUUUUUUUUUUUUUUUUUUUUUUUUUUUUUU-3'

For the synthesis of the uridine 40-mer in this Example, a CPG solid phase carrier wherein 2'-O-tert-butyldimethylsilyl-5'-O-(4,4'-dimethoxytrityl)uridine is linked by a linker was used as a solid phase carrier. Furthermore, 5'-O-(4,4'-dimethoxytrityl)-2'-O-(2-cyanoethoxymethoxymethyl)uridine 3'-O-(2-cyanoethyl N,N-diisopropylphosphoramidite), i.e., uridine EMM amidite (1009), was used as a nucleic acid monomer compound, 5-benzylmercapto-1H-tetrazole was used as a condensing agent, an iodine solution was used as an oxidant, and a phenoxyacetic acid solution and a N-methylimidazole solution were used as capping solutions. Under these conditions, the aforementioned nucleic acid monomer compound was condensed 39 times, the 5' terminal hydroxyl group was deprotected on the solid phase, and cleavage from the CPG solid phase carrier and deprotection of each phosphoric acid site were performed using conc. aqueous ammonia-ethanol mixture (3:1) at 40° C. for 4 hr. The thus-obtained reaction mixture was concentrated under reduced pressure and reacted in a solution of 1M tetrabutylammoniumfluoride in DMSO containing 0.67% nitromethane at 30° C. for 4 hr to deprotect the 2'-position hydroxyl group. Ethanol was added to the thus-obtained solution to allow precipitation, and the precipitate was dissolved in water for injection to give an aqueous solution containing the object compound (uridine 40-mer).

Figure 2:
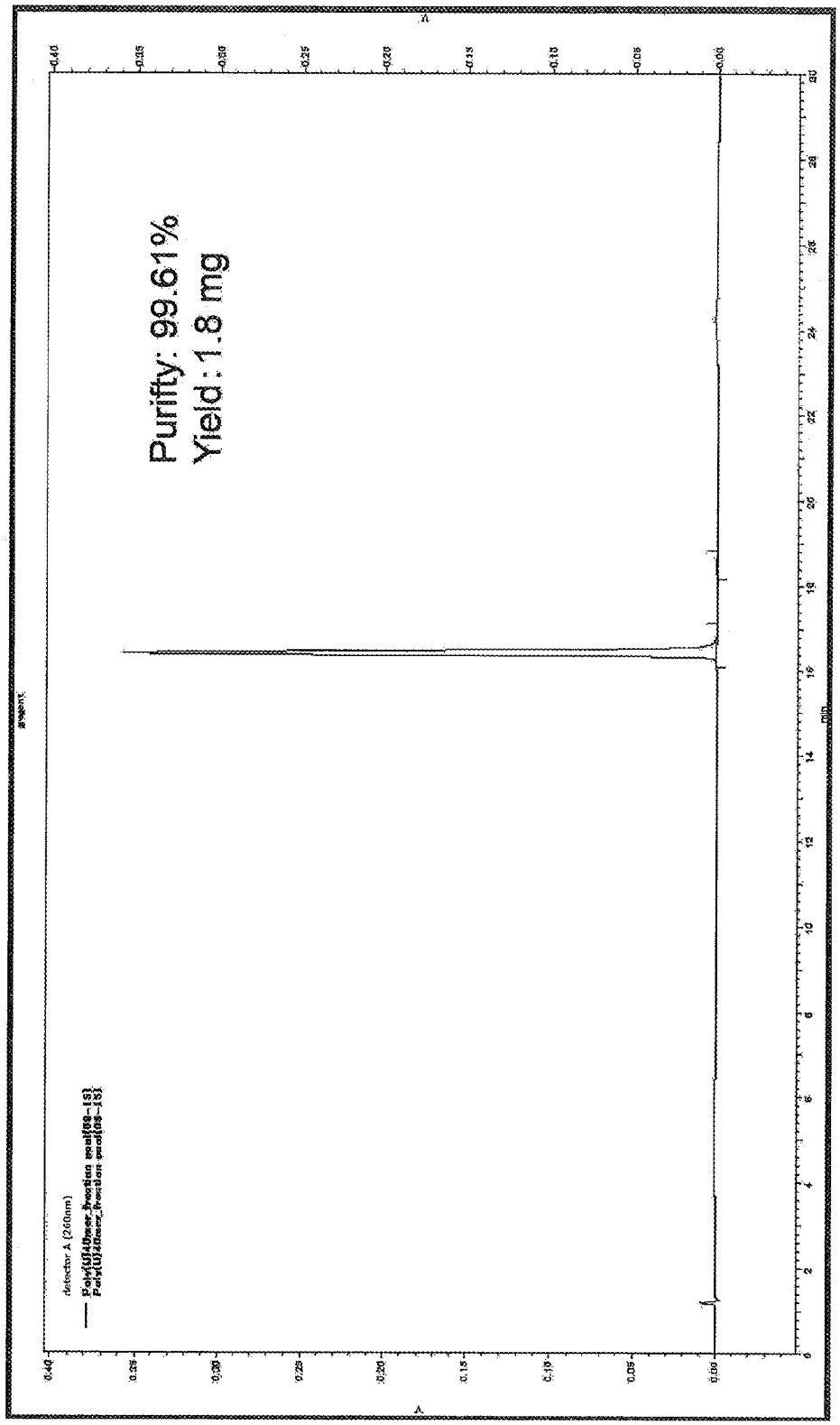
FIG. 2 is an HPLC chart of the nucleic acid (after purification) produced in Example 6.
Figure 3:
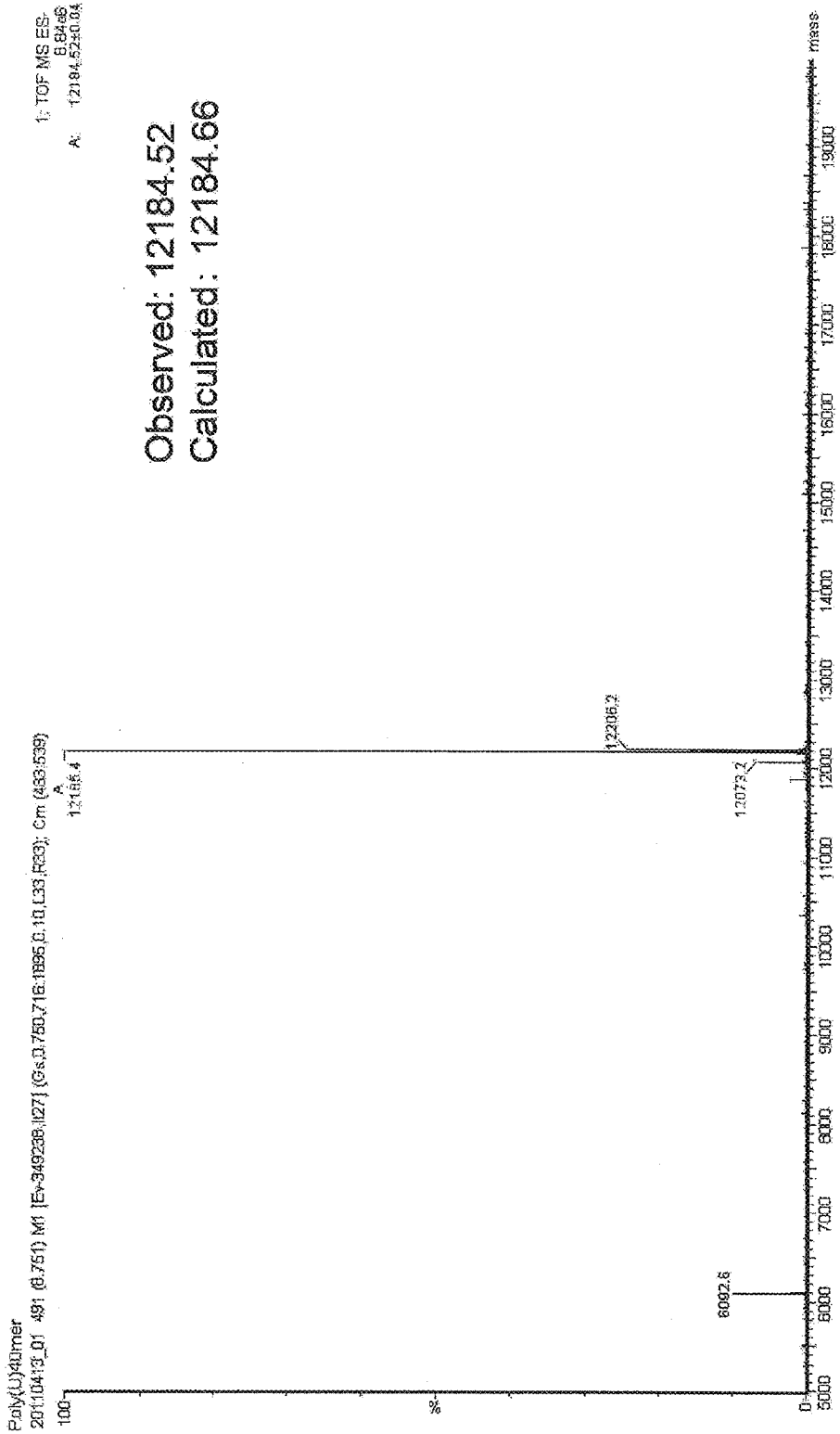
FIG. 3 is a mass spectrum of the nucleic acid (after purification) produced in Example 6.

The analysis results of the uridine 40-mer obtained above by HPLC are shown in FIG. 1. As shown in the Figure, since an almost single sharp peak was obtained, it was suggested that the object 40-mer was obtained with high purity. The purity of the uridine 40-mer calculated based on the peak intensity of FIG. 1 was 74.64% (mass ratio) as shown in the Figure. In addition, the main peak part was separated and purified by HPLC and analyzed again by HPLC. The results are shown in FIG. 2. As shown in the Figure, since the peak intensity of the impurity further decreased as compared to FIG. 1, it was suggested that the purity of the object 40-mer became higher. The purity of the uridine 40-mer calculated based on the peak intensity in FIG. 2 was 99.61% (mass ratio) as shown in the Figure. In addition, the results of the mass spectrometry (mass spectrum chart) of this reaction mixture are shown in FIG. 3. As shown in the Figure, the molecular ion peak of molecular weight 12184.52 was observed. Since this molecular weight matched well with the calculated value (12184.66) of the molecular weight of the object uridine 40-mer (U40mer), it was confirmed that the object uridine 40-mer (U40mer) was obtained.

The HPLC analysis of the uridine 40-mer (U40mer) was performed using an instrument (HPLC system) of SHIMADZU CORPORATION, and the mass spectrometry was performed using an instrument of Waters (SYNAPT G2 (trade name)). Furthermore, oligomer synthesis using cytidine EMM amidite (1C$^{Ac}$) (or (1014)), adenosine EMM amidite (1A$^{Ac}$) or guanosine EMM amidite (1 G$^{Pac}$) could also be performed in the same manner as in the synthesis of the uridine 40-mer (U40mer).

Example 7

Synthesis of RNA Using 4 Kinds of EMM Amidites

Using 4 kinds of EMM amidites of the uridine EMM amidite (1009) synthesized in Example 2, the cytidine EMM amidite (1014) synthesized in Example 3, the adenosine EMM amidite (1019) synthesized in Example 4, and the guanosine EMM amidite (1024) synthesized in Example 5, RNAs shown by the following SEQ ID NOs: 2-4 were synthesized.

(SEQ ID NO: 2)
5'-AUACUAUUCGACACGCGAAGUUCCCCACACCGGAACUUCGCGU
GUCGAAUAGUAUUCUUCGG-3'

(SEQ ID NO: 3)
5'-AGCAGCUGUACAUUGACUUUAGCCCCACACCGGCUAAAGUCAA
UGUACAGCUGCUUCUUCGG-3'

(SEQ ID NO: 4)
5'-CUUCGCGUGUCGAAUAGUAUU-3'

In the same manner as in Example 6 except that 4 kinds of the EMM amidites of the uridine EMM amidite (1009), cytidine EMM amidite (1014), adenosine EMM amidite (1019) and guanosine EMM amidite (1024) were used as nucleic acid monomer compounds, synthesis in this Example was performed. More specifically, instead of the 39 times of condensation of the uridine EMM amidite (1009), the aforementioned 4 kinds of the EMM amidites were condensed from the 3' side to the 5' side in given number of times (61 times in the syntheses of SEQ ID NOs: 2 and 3, 20 times in the synthesis of SEQ ID NO: 4) according to any of SEQ ID NOs: 2-4. All conditions other than this were the same as those in Example 6.

RNAs of SEQ ID NOs: 2-4 synthesized in the above were each analyzed by HPLC. As a result, a mostly single, sharp peak was obtained in all of them. This suggests that the object RNAs of SEQ ID NOs: 2-4 were obtained with high purity. The analysis results of the aforementioned HPLC are shown in more detail in the following.

The purity of the RNA of SEQ ID NO: 2 synthesized above was calculated based on the peak intensity ratio of the aforementioned HPLC and found to be 84.27% (mass ratio). This numerical value shows the synthesis yield of EMM amidite subjected to 61 times of condensation reaction. That is, the synthesis yield of a single condensation reaction was as high as about 99.72% (mass ratio). According to the mass spectrometry of the reaction mixture, a molecular ion peak of the molecular weight of 19756.13 was observed. This molecular weight matched well with the calculated value (19755.71) of the molecular weight of RNA shown by SEQ ID NO: 2. Therefrom it was confirmed that the object RNA of SEQ ID NO: 2 was obtained. Furthermore, the main peak part of the aforementioned HPLC was separated and purified and analyzed again by HPLC. As a result, since the peak intensity of the impurity further decreased, it was suggested that the purity of the object RNA of SEQ ID NO: 2 became higher. The purity of the RNA of SEQ ID NO: 2 calculated based on the peak intensity ratio after the aforementioned separation and purification of the main peak was 96.47% (mass ratio).

Moreover, the purity of the RNA of SEQ ID NO: 3 synthesized above was calculated based on the peak intensity ratio of the aforementioned HPLC and found to be 79.65% (mass ratio). This numerical value shows the synthesis yield of EMM amidite subjected to 61 times of condensation reaction. That is, the synthesis yield of a single condensation reaction was as high as about 99.63% (mass ratio). According to the mass spectrometry of the reaction mixture, a molecular ion peak of the molecular weight of 19755.70 was observed. This molecular weight matched well with the calculated value (19755.71) of the molecular weight of RNA shown by SEQ ID NO: 3. Therefrom it was confirmed that the object RNA of SEQ ID NO: 3 was obtained. Furthermore, the main peak part of the aforementioned HPLC was separated and purified and analyzed again by HPLC. As a result, since the peak intensity of the impurity further decreased. The purity of the RNA of SEQ ID NO: 3 calculated based on the peak intensity ratio after the aforementioned separation and purification of the main peak was 95.37% (mass ratio), and the purity was higher than that before the aforementioned separation and purification of the main peak.

Moreover, the purity of the RNA of SEQ ID NO: 4 synthesized above was calculated based on the peak intensity ratio of the aforementioned HPLC and found to be 86.67% (mass ratio). According to the mass spectrometry of the reaction mixture, a molecular ion peak of the molecular weight of 6650.69 was observed. This molecular weight matched well with the calculated value (6650.94) of the molecular weight of RNA shown by SEQ ID NO: 4. Therefrom it was confirmed that the object RNA of SEQ ID NO: 4 was obtained. Furthermore, the main peak part was separated and purified by HPLC. As a result, the RNA of SEQ ID NO: 4 could be obtained with still higher purity.

As mentioned above, according to this Example, it was confirmed that RNA of any sequence can be synthesized using plural kinds of EMM amidite corresponding to plural kinds of bases. The measurement devices used for HPLC and MS were the same as those in Example 6.

While the present invention has been explained by referring to the embodiments, the present invention is not limited by the above-mentioned embodiments. The constitution and detail of the present invention can be variously changed within the scope of the present invention as long as those of ordinary skill in the art can understand.

This application is based on a patent application No. 2011-184196 filed in Japan (filing date: Aug. 25, 2011), the contents of which are incorporated in full herein.

INDUSTRIAL APPLICABILITY

As explained above, according to the glycoside compound, the production method of thioether, ether, the production method of ether, and the production method of the glycoside compound of the present invention, a phosphoramidite, which can be produced at a low cost and can produce a nucleic acid in a high yield and with high purity can be provided. In addition, according to the production method of a nucleic acid of the present invention, a nucleic acid can be produced in a high yield and with high purity using the aforementioned phosphoramidite. The use of the aforementioned thioether, ether, glycoside compound, and nucleic acid produced by the present invention is not particularly limited, and they can be used for a wide range of use. According to the present invention, for example, they can be preferably used as pharmaceutical products or synthesis intermediates therefor, since they can be obtained at a low cost, in a high yield, with high purity.

The invention claimed is:

1. An ether represented by the following chemical formula (106):

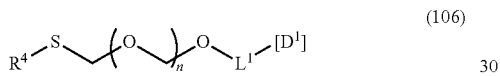

(106)

in the aforementioned chemical formula (106), $R^4$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, n is a positive integer, $L^1$ is an ethylene group (—$CH_2CH_2$—), wherein hydrogen atoms besides a hydrogen atom bonded to the α-position relative to [$D^1$] are optionally substituted by a straight chain or branched alkyl group, and

[$D^1$] is an electron-withdrawing group, an enantiomer thereof, a tautomer or stereoisomer thereof or a salt thereof.

2. A method of producing the ether according to claim 1, comprising a coupling reaction of a thioether represented by the following chemical formula (103) and an alcohol represented by the following chemical formula (105), in the presence of a halogenating agent and a Lewis acid,

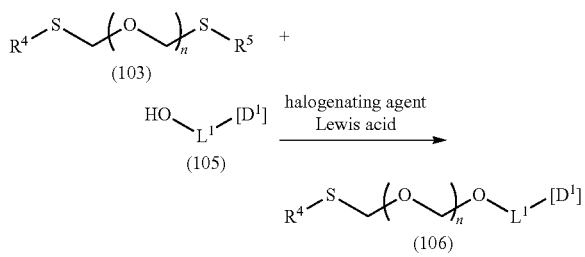

in the aforementioned chemical formulas (103) and (105), $R^4$ is as defined for the aforementioned chemical formula (106), $R^5$ is a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same as or different from $R^4$, in the aforementioned chemical formula (103), n is as defined for the aforementioned chemical formula (106), and in the aforementioned chemical formula (105), $L^1$ and [$D^1$] are as defined for the aforementioned chemical formula (106).

3. The production method according to claim 2, wherein the aforementioned halogenating agent is at least one selected from the group consisting of N-chlorosuccinimide, N-bromosuccinimide, N-iodosuccinimide, iodine, bromine and chlorine.

4. The production method according to claim 2, wherein the aforementioned Lewis acid is at least one selected from the group consisting of perfluoroalkylcarboxylic acid, perfluoroalkylsulfonic acid, alkylsulfonic acid and a salt thereof.

5. The production method according to claim 2, wherein the aforementioned Lewis acid is a silver salt of trifluoromethanesulfonic acid.

6. The production method according to claim 2, wherein the aforementioned coupling reaction is performed in the co-presence of molecular sieve.

7. The production method according to claim 6, further comprising a step of producing the thioether represented by the chemical formula (103) by the production method comprising a coupling reaction of thiol or thioalkoxide represented by the chemical formulas (101a) and (101b) with a halide represented by the chemical formula (102) to give a thioether represented by the chemical formula (103):

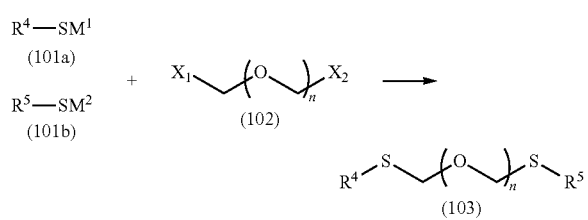

wherein
in the aforementioned chemical formulas (101a), (101b) and (103), $R^4$ and $R^5$ are each a hydrocarbon group, a straight chain or branched alkyl group, a straight chain or branched alkenyl group, a straight chain or branched alkynyl group, an aryl group, a straight chain or branched arylalkyl group, a cycloalkyl group, a cycloalkenyl group, a straight chain or branched cycloalkylalkyl group, a straight chain or branched cyclylalkyl group, or a straight chain or branched alkoxyalkyl group, which may be the same or different, in the aforementioned chemical formulas (101a) and (101b), $M^1$ and $M^2$ may be the same or different and each is a hydrogen atom or a metal, in the aforementioned chemical formulas (102) and (103), n is a positive integer, and in the aforementioned chemical formula (102), $X^1$ and $X^2$ may be the same or different and each is halogen.

8. The production method according to claim 7, wherein, in the aforementioned chemical formulas (101a), (101b) and (103), $R^4$ and $R^5$ are each a methyl group.

* * * * *